United States Patent
Hernandez

(10) Patent No.: US 12,178,656 B2
(45) Date of Patent: *Dec. 31, 2024

(54) SYSTEM AND METHOD OF TRIGGERING NON-INVASIVE CONTINUOUS ECHOCARDIOGRAPHIC MONITORING

(71) Applicant: Lazaro Eduardo Hernandez, Cooper City, FL (US)

(72) Inventor: Lazaro Eduardo Hernandez, Cooper City, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/651,196

(22) Filed: Apr. 30, 2024

(65) Prior Publication Data

US 2024/0277319 A1    Aug. 22, 2024

Related U.S. Application Data

(63) Continuation-in-part of application No. 18/471,150, filed on Sep. 20, 2023, which is a continuation-in-part
(Continued)

(51) Int. Cl.
*A61B 8/00* (2006.01)
*A61B 8/08* (2006.01)

(52) U.S. Cl.
CPC .......... *A61B 8/5223* (2013.01); *A61B 8/4483* (2013.01); *A61B 8/461* (2013.01); *A61B 8/488* (2013.01); *A61B 8/54* (2013.01)

(58) Field of Classification Search
CPC ......... A61B 8/02; A61B 8/4281; A61B 8/461; A61B 8/4236; A61B 8/12; A61B 8/4494
See application file for complete search history.

(56) References Cited

U.S. PATENT DOCUMENTS

| 5,090,410 A | 2/1992 | Saper et al. |
| 5,345,935 A | 9/1994 | Hirsch et al. |

(Continued)

FOREIGN PATENT DOCUMENTS

| WO | 2007124126 A3 | 10/2008 |
| WO | 2009089183 A1 | 7/2009 |
| WO | 2012005989 A3 | 4/2012 |

OTHER PUBLICATIONS

GE Vivid q Portable Cardiac Ultrasound, retrieved from internet, retrieved on Sep. 26, 2022, <URL: https://www.ultrasoundsupply.com/products/ultrasound-machines/ge-ultrasound/ge-vivid-q-portable/>.

(Continued)

*Primary Examiner* — Amal Aly Farag

(57) ABSTRACT

A system and a method of non-invasive continuous echocardiographic monitoring is provided with an ultrasound transducer and a bedside monitor. The beside monitor includes a monitor central processing unit (CPU). First, the ultrasound transducer is attached onto a specific skin portion of a patient. The specific skin portion is positioned adjacent to a patient's heart. Next, continuous echocardiographic data is sensed with the ultrasound transducer. After relaying the continuous echocardiographic data from the ultrasound transducer to the monitor CPU, the monitor CPU generates a real-time ultrasound image of the heart from the continuous echocardiographic data. Finally, the real-time ultrasound image is outputted with the bedside monitor. If the bedside monitor has a main screen, then the real-time ultrasound image is displayed through a picture-in-picture format with the main screen. Otherwise, if the beside monitor has an ancillary screen, then the real-time ultrasound image is exclusively displayed with the ancillary screen.

27 Claims, 28 Drawing Sheets

Related U.S. Application Data of application No. 17/935,505, filed on Sep. 26, 2022, now Pat. No. 11,957,505, which is a continuation-in-part of application No. 17/210,013, filed on Mar. 23, 2021, now Pat. No. 11,457,889.

(60) Provisional application No. 63/141,465, filed on Jan. 25, 2021.

(56) References Cited

U.S. PATENT DOCUMENTS

| | | |
|---|---|---|
| 5,758,652 A | 6/1998 | Nikolic |
| 6,117,105 A | 9/2000 | Bresnaham et al. |
| 6,186,955 B1 | 2/2001 | Baura |
| 6,514,207 B2 | 2/2003 | Ebadollahi et al. |
| 7,666,144 B2 | 2/2010 | Cohen |
| 8,070,685 B2 | 12/2011 | Harhen et al. |
| 8,463,361 B2 | 6/2013 | Tupin, Jr. |
| 2003/0013959 A1 | 1/2003 | Grunwald et al. |
| 2004/0111045 A1 | 6/2004 | Sullivan et al. |
| 2006/0122548 A1 | 6/2006 | Abrams |
| 2006/0173307 A1 | 8/2006 | Amara et al. |
| 2007/0016019 A1 | 1/2007 | Salgo |
| 2008/0004904 A1 | 1/2008 | Tran |
| 2008/0312562 A1 | 12/2008 | Routh et al. |
| 2009/0299155 A1 | 12/2009 | Yang |
| 2011/0118562 A1 | 5/2011 | Smith et al. |
| 2013/0041252 A1 | 2/2013 | Vignon et al. |
| 2015/0011846 A1 | 1/2015 | Chang |
| 2015/0164468 A1 | 6/2015 | Ahn et al. |
| 2016/0303307 A1 | 10/2016 | Madjarov et al. |
| 2017/0124700 A1 | 5/2017 | Sarojam et al. |
| 2018/0132829 A1 | 5/2018 | Park et al. |
| 2018/0333050 A1 | 11/2018 | Greiner et al. |
| 2019/0343484 A1 | 11/2019 | Rothberg et al. |
| 2020/0121199 A1 | 4/2020 | Freeman et al. |
| 2020/0397313 A1 | 12/2020 | Attia et al. |

OTHER PUBLICATIONS

GE Vivid S6 Cardiovascular Ultrasound, retrieved from internet, retrieved on Sep. 26, 2022, <URL: https://www.ultrasoundsupply.com/products/ultrasound-machines/ge-ultrasound/ge-vivid-s6/>.

Mindray M5 Portable Ultrasound Machine, retrieved from internet, retrieved on Mar. 23, 2021, <URL: https://www.mindray.com/au/product/M5_OB.html.

SYSTEM AND METHOD OF TRIGGERING NON-INVASIVE CONTINUOUS ECHOCARDIOGRAPHIC MONITORING

The current application is a continuation-in-part (CIP) application of the U.S. non-provisional application Ser. No. 18/471,150 filed on Sep. 20, 2023. The U.S. non-provisional application Ser. No. 18/471,150 is a CIP application of the U.S. non-provisional application Ser. No. 17/935,505 filed on Sep. 26, 2022. The U.S. non-provisional application Ser. No. 17/935,505 is a CIP application of the U.S. non-provisional application Ser. No. 17/210,013 filed on Mar. 23, 2021. The U.S. non-provisional application Ser. No. 17/210,013 claims a priority to the U.S. Provisional Patent application Ser. No. 63/141,465 filed on Jan. 25, 2021.

FIELD OF THE INVENTION

The present invention generally relates to an echocardiographic device. More specifically, the present invention provides an ultrasound transducer that can be positioned and secured to a patient's chest and in contact with the patient's skin, while obtaining a continuous ultrasound image of the patient's heart without interruption from movement by the patient.

BACKGROUND OF THE INVENTION

Upon arrival to intensive care unit or emergency department, any patient in critical conditions is hooked up to multiple medical devices to track vital parameters on a bedside monitor. These devices typically include pulse oximetry to monitor the oxygen saturation in the body, electrocardiogram to monitor the heart rate and heart rhythm, chest motion sensors to monitor the respiratory rate, and thermometer to monitor temperature. If the patient has a catheter inside any vein or artery, a pressure wave is also displayed demonstrating the central venous and central arterial pressure, respectively.

Echocardiography is not utilized as a continuous monitoring of the heart. When a heart problem is suspected in a critically ill patient, the physician orders an echocardiogram, which is performed by a cardiac sonographer by using a commercially existing portable ultrasound machine. The ultrasound machine is wheeled from the echo station to the patient's bedside. The cardiac sonographer by holding a cardiovascular ultrasound transducer in his/her hand is capable to obtain, display, and record the image of the heart in the machine's hard drive and subsequently export them to the imaging server for further visualization, analysis, and interpretation by the imaging cardiologist using a reading station installed in a personal computer.

Currently, there is no technology to directly display a cardiac ultrasound image of the patient's heart in the standard patient monitor at the bedside. If an echocardiographic image is deemed necessary for assessing a patient's cardiac status, a technician must be called to perform the echocardiogram using a standard echo machine.

Therefore, an objective of the present invention is to allow limited real time, ongoing display of a patient's heart at the bedside for rapid assessment of possible cardiac emergencies (e.g., tamponade, intracardiac thrombi, cardiac function, and fluid status) without the need for a cardiac sonographer or a standard echocardiographic machine. The present invention is not designed as a substitute for a complete echocardiographic study performed by a sonographer using a standard echocardiographic machine which would provide more detailed evaluation of cardiac anatomy and function when needed for patient management.

Upon arrival to any intensive care unit or emergency department, any patient in critical condition, would be connected to the present invention, which would be in contact with the patient's skin coupled with ultrasound gel and connected to the patient's bedside monitor by a coaxial cable to obtain an ultrasound image in real time without the need of any commercially existing ultrasound machine/device. Another objective of the present invention is to be available as an additional display incorporated into the standard bedside monitors currently utilized in intensive care units or emergency departments using a picture in picture technology or onto an accessory monitor attached to the standard one. Another objective of the present invention is to calculate a left ventricular ejection fraction which would trigger an alarm (within parameters preset by the bedside physician) turning it into a potentially lifesaving imaging device.

The present invention also provides a tremendous diagnostic value in critical hours (nights and weekends) when the cardiac sonographers and imaging cardiologists are not available in the hospital (on-call). What could now take about 3 hours (cardiac sonographer must drive to the hospital and wheel the ultrasound machine to the bedside to obtain the images and export them to be analyzed by the reading cardiologist), the heart could be evaluated immediately with the present invention. Consequently, no cardiac sonographer is needed to hook up the transducer to the patient's chest. Once the patient arrives to the intensive care unit or emergency room, the present invention can be positioned on the patient's chest by any medical practitioner and secured with adhesive pads once a 4-chamber view of the heart is visualized. In addition, no cardiac sonographer is needed to obtain, display, or record the image of the heart. The present invention allows this to occur in an automatic fashion (by device programming) or by pressing a button in the patient's monitor. Moreover, no imaging cardiologist is necessary for imaging interpretation or reporting. The intensive care unit or emergency department physician would be able to visualize and analyze the image of the heart at any time and make changes to the patient's management, accordingly.

The present invention can also be utilized to display a continuous image of the heart during catheter interventional procedures without the need of a cardiac sonographer and a conventional ultrasound machine. This will lead to: 1.) more efficient time utilization of cardiac sonographers who currently may be required to remain on standby in the cardiac catheterization laboratory for hours while a procedure is performed; 2.) a decrease of personnel in the catheterization laboratory leading to reduced risk of infection; and 3.) reduce the space needed in the catheterization lab to accommodate the conventional portable ultrasound machine.

Based on real-world experience, most echocardiograms ordered in an intensive care unit or emergency department are focused on assessment or follow-up cardiac function, pericardial effusion (fluid around the heart), intracardiac thrombus/vegetation and intracardiac volume. However, the present invention allows a medical practitioner to assess those parameters instantaneously at the bedside decreasing the need for repeated echocardiograms and the consequent cost. Thus, the present invention is an addition to the monitoring devices currently available in any intensive care unit or emergency room.

SUMMARY OF THE INVENTION

The present invention is a novel cardiovascular ultrasound transducer, central processing unit (CPU), and display for continuous and non-invasive ultrasound monitoring of the heart mainly conceived for patients in intensive care unit or emergency department without the need of a cardiac sonographer and conventional/commercially available ultrasound machine.

The main value of the present invention is to continuously (24 hours monitoring if necessary) and non-invasively monitor a moving image of the heart in a critically ill patient in any intensive care unit or emergency department by applying the already existing ultrasound technology into a newly designed cardiovascular ultrasound transducer and monitor intended to be available at bedside in each intensive care unit and emergency department. The image would be shown as an additional display incorporated into the standard bedside monitors currently utilized in intensive care units or emergency departments using a picture in picture technology or onto an accessory monitor attached to the standard one. The displayed echo image would be in addition to the currently available monitoring parameters. Moreover, the present invention does not use the current and commercially available ultrasound equipment/devices.

DETAILED DESCRIPTION OF THE INVENTION

All illustrations of the drawings are for the purpose of describing selected versions of the present invention and are not intended to limit the scope of the present invention.

Figure 1:
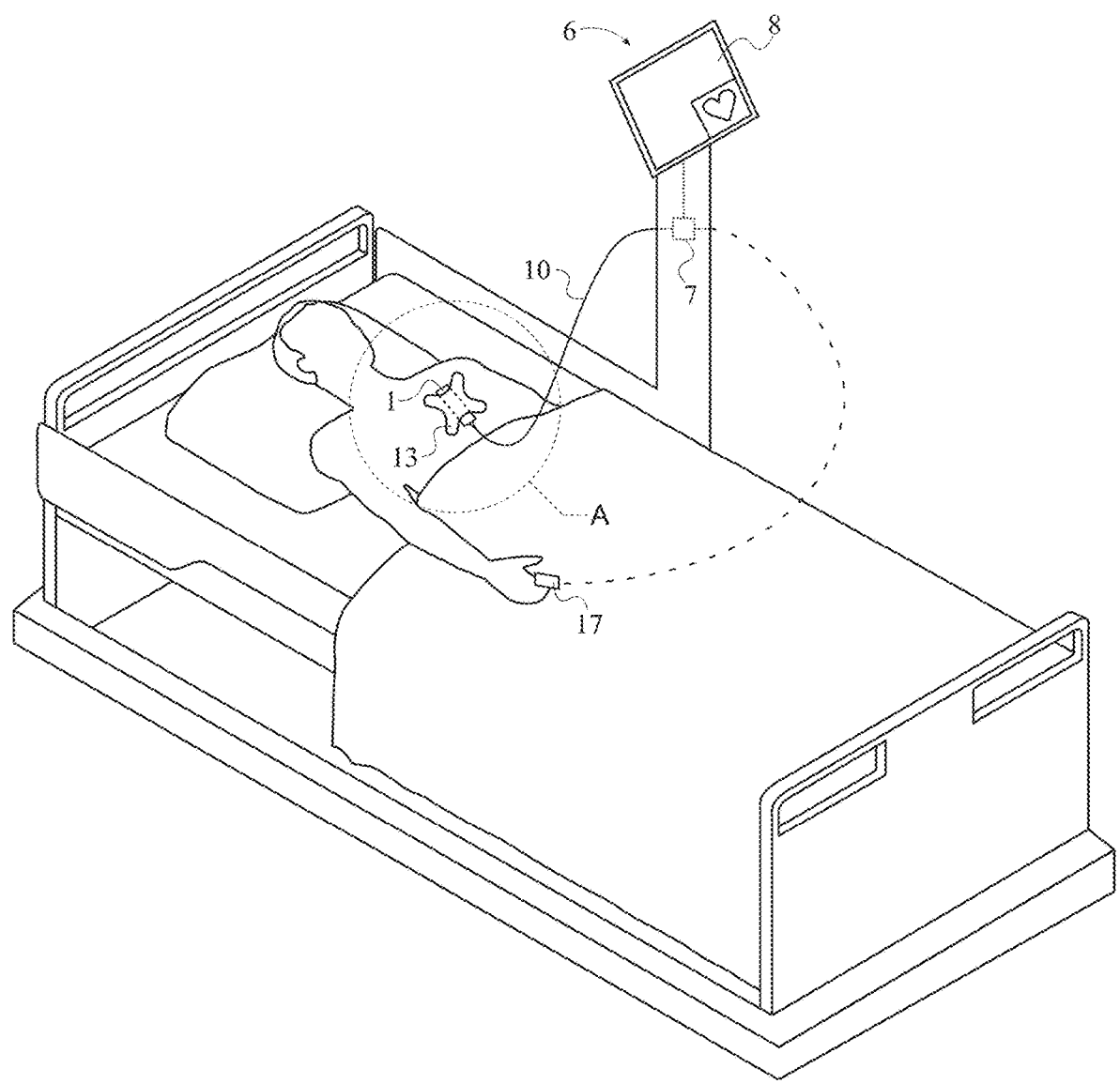
FIG. 1 is an illustration depicting for the system of the present invention, wherein the main screen the bedside monitor uses to display the real-time ultrasound image.
Figure 2:
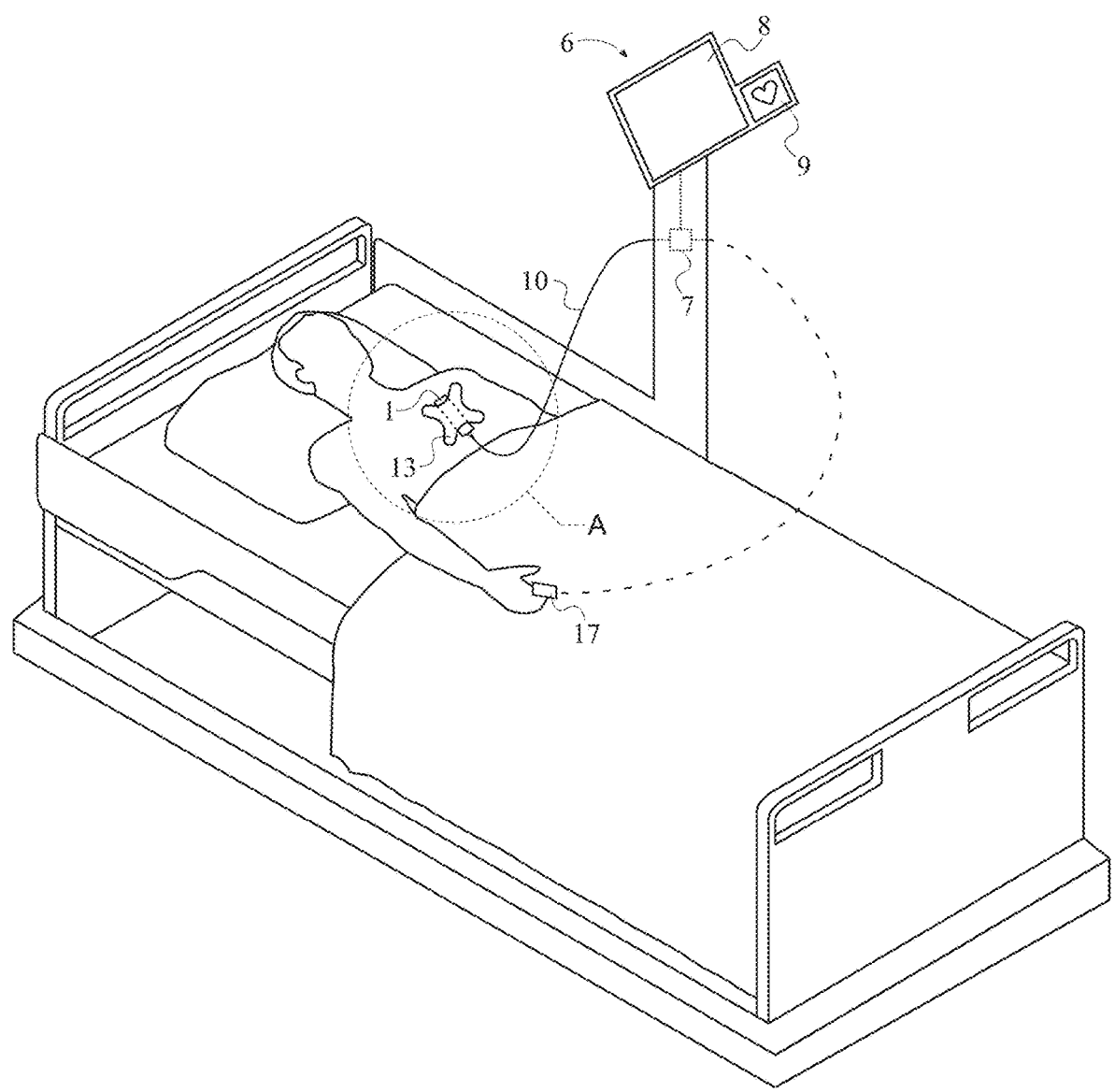
FIG. 2 is another illustration depicting for the system of the present invention, wherein the bedside monitor alternatively uses the ancillary screen to display the real-time ultrasound image.

The present invention is a system and a method of non-invasive continuous echocardiographic monitoring of a patient. The present invention is not meant to replace a comprehensive echocardiographic assessment but is meant to guide bedside patient management. The present invention allows an operator to rapidly assess for any possible cardiac emergencies (e.g., tamponade, intracardiac thrombi, cardiac function, and fluid status). The system used to implement the method of the present invention is provided with an ultrasound transducer 1 and a bedside monitor 6 (Step A), which is shown in FIGS. 1 and 2. The ultrasound transducer 1 is used to image an interior portion of a patient's body by using a technique known as ultrasonography. The bedside monitor 6 allows a medical practitioner to readily view a patient's vitals and any other important medical information about the patient. The bedside monitor 6 is preferably a kind of computing kiosk but can alternatively be a desktop, a laptop, a mobile personal computing (PC) device (e.g., a "smartphone"), or a tablet PC device that is in wireless or wired communication with the other components of the system used to implement the method of the present invention. Moreover, the bedside monitor 6 includes a monitor central processing unit (CPU) 7, which is used to process data received by the bedside monitor 6 and is used to manage different functionalities of the bedside monitor 6.

Figure 7:
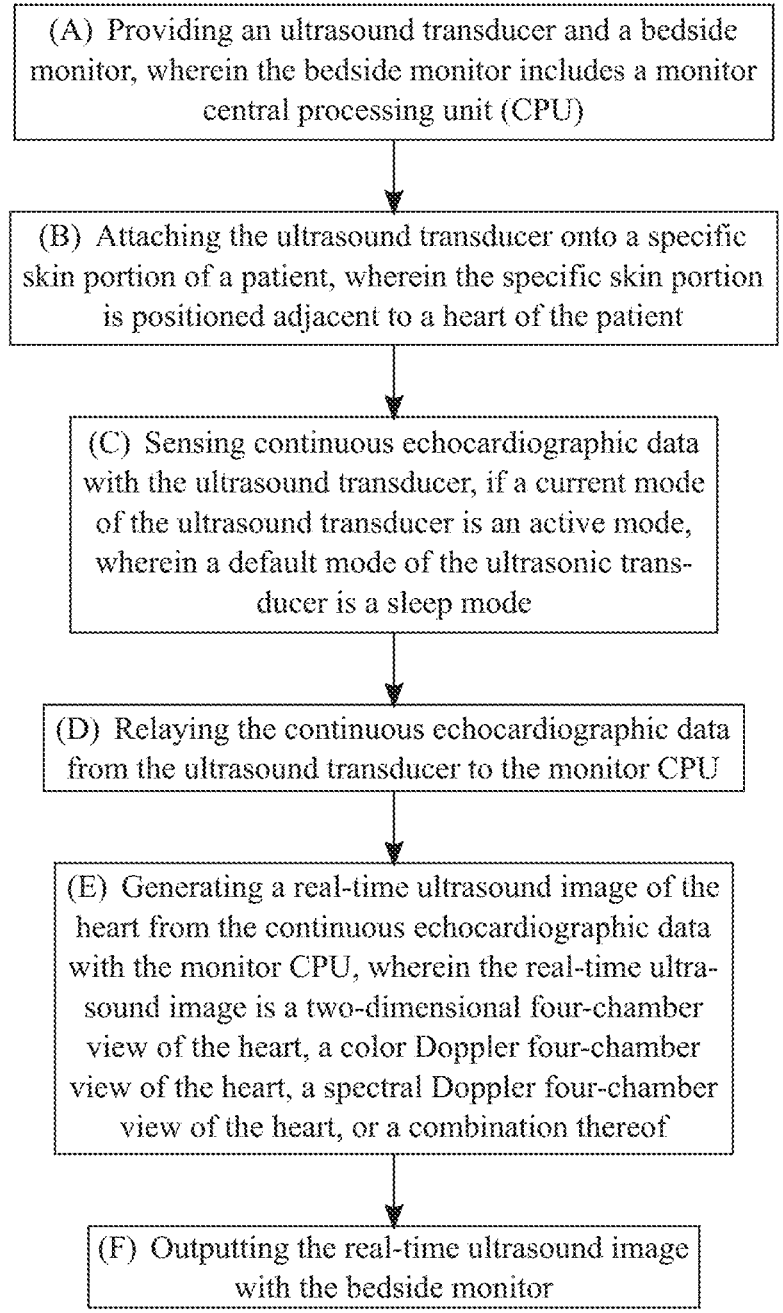
FIG. 7 is a flowchart depicting an overall process for the method of the present invention.

As can be seen in FIG. 7, the overall process followed by the method of the present invention allows for ultrasound monitoring of a patient's heart without the need of a cardiac sonographer or a conventional ultrasound machine. The overall process begins by attaching the ultrasound transducer 1 onto a specific skin portion 11 of a patient (Step B). The patient would typically be someone that is critically ill and is laying in a hospital bed, adjacent to the bedside monitor 6. The specific skin portion 11 is positioned adjacent to the patient's heart and is the optimal location on the patient's skin to place the ultrasound transducer 1. The overall process continues by sensing continuous echocardiographic data with the ultrasound transducer 1 (Step C). The continuous echocardiographic data is used to track the live movement of the patient's heart. In some embodiments of the present invention, Step C is only executed if a current mode of the ultrasound transducer is an active mode, wherein a default mode of the ultrasonic transducer is a sleep mode. When the ultrasonic transducer is activated and is readily available to collect measurement data, the ultrasonic transducer is in its active mode. When the ultrasonic transducer is deactivated (e.g., a kind of power-saving mode) and is not readily available to collect measurement data, the ultrasonic transducer is in its sleep mode. The continuous echocardiographic data is then relayed from the ultrasound transducer 1 to the monitor CPU 7 (Step D), which allows the monitor CPU 7 to access and process the continuous echocardiographic data. The overall process continues by generating a real-time ultrasound image of the patient's heart from the continuous echocardiographic data with the monitor CPU 7 (Step E). The real-time ultrasound image is a visual representation of the continuous echocardiographic data and acts as a live feed to view the patient's heart. In addition, the real-time ultrasound image can be, but is not limited to, a two-dimensional four-chamber view of the patient's heart, a color Doppler four-chamber view of the patient's heart, a spectral Doppler four-chamber view of the patient's heart, or a combination thereof. The overall process concludes by outputting the real-time ultrasound image with the bedside monitor 6 so that a medical practitioner can readily view the patient's heart for any ailments or abnormalities.

Figure 6:
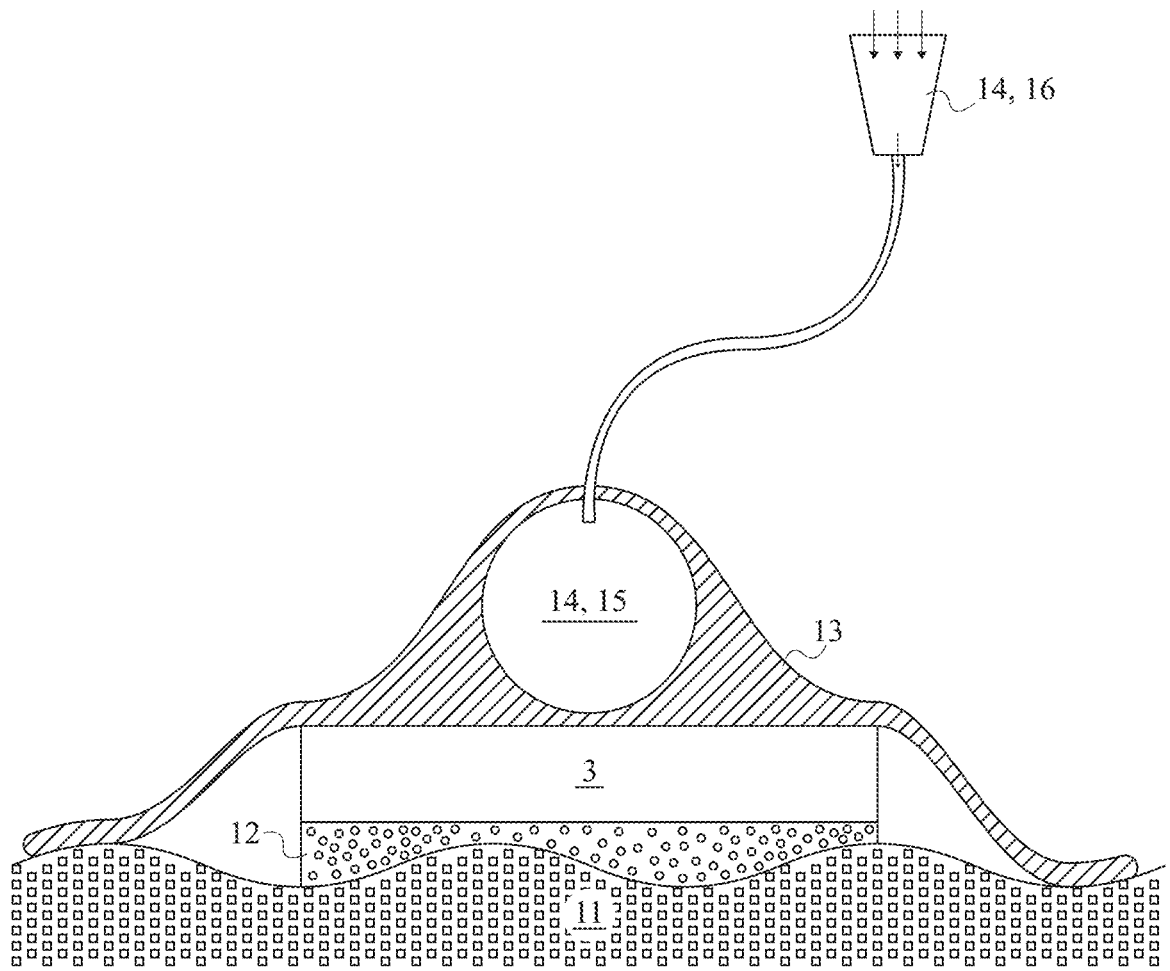
FIG. 6 is a cross-sectional schematic view taken either along line B-B in FIG. 4 or along line B-B in FIG. 5, which depicts the ultrasound transducer being attached onto the patient's skin.
Figure 8:
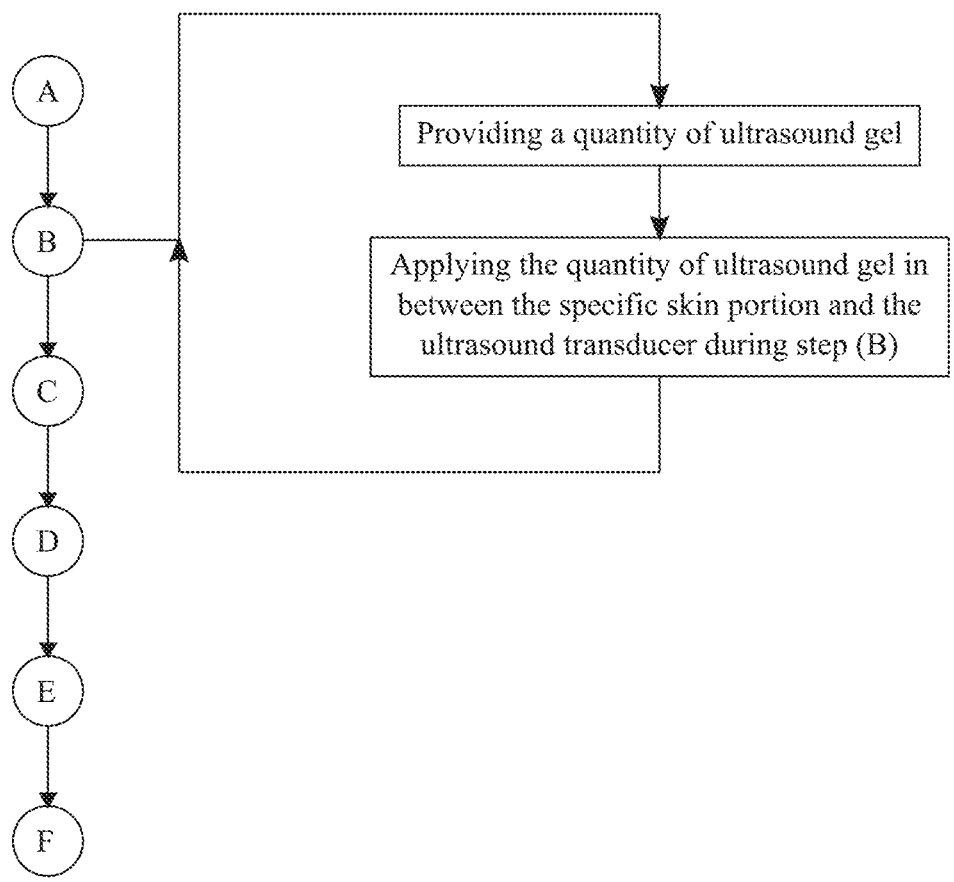
FIG. 8 is a flowchart depicting a subprocess for using a quantity of ultrasound gel with the ultrasound transducer.

As can be seen in FIGS. 6 and 8, one subprocess for the method of the present invention provides a quantity of ultrasound gel 12, which is used to eliminate air pockets between the specific skin portion 11 and the ultrasound transducer 1. Thus, the quantity of ultrasound gel 12 is applied in between the specific skin portion 11 and the ultrasound transducer 1 during Step B. Consequently, emitted acoustic waves can better travel from the ultrasound transducer 1 into the specific skin portion 11, and reflected acoustic waves can better travel from the specific skin portion 11 into the ultrasound transducer 1. This reduces noise in the continuous echocardiographic data and eventually produces the real-time ultrasound image with a better quality.

Figure 3:
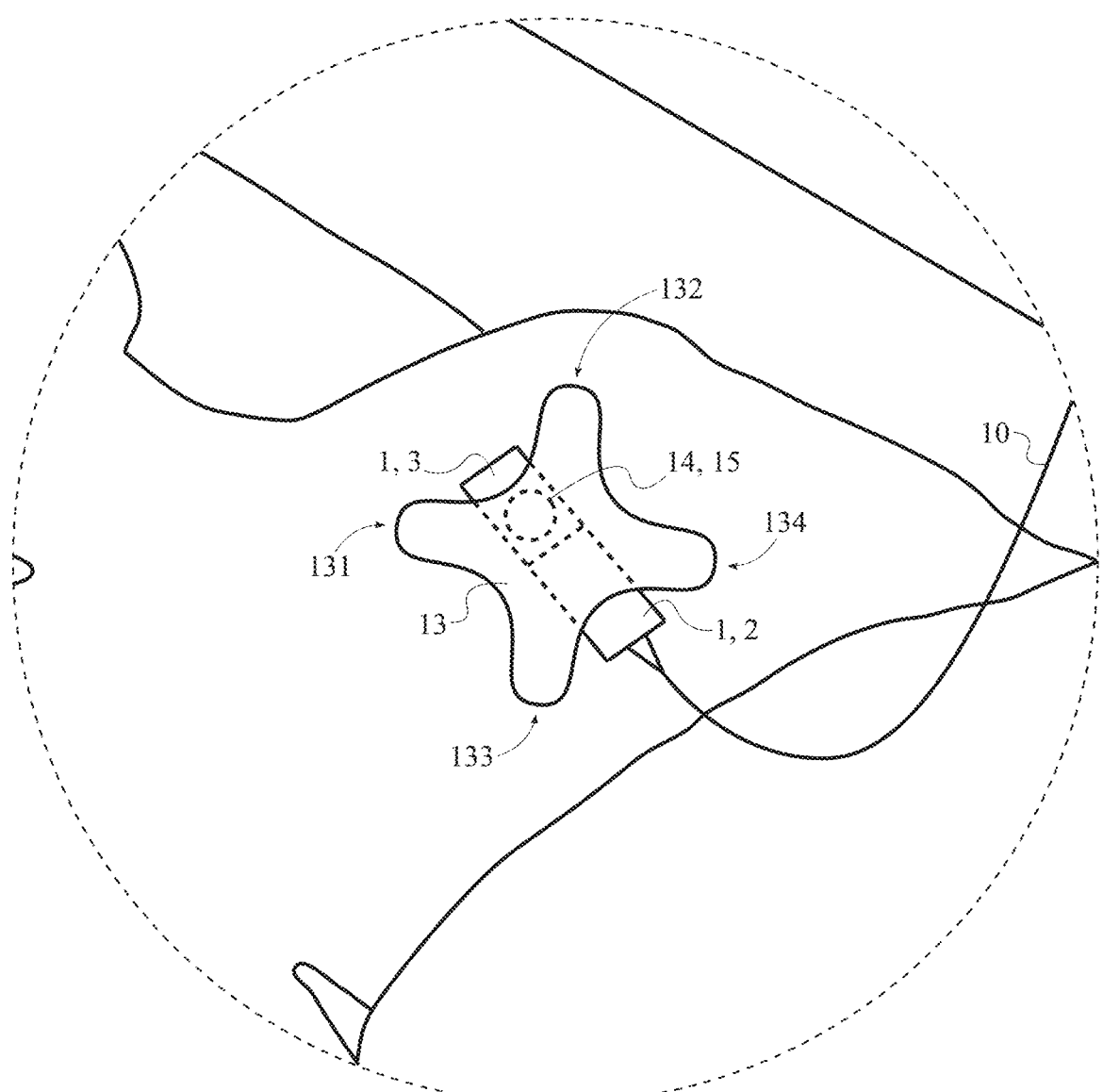
FIG. 3 is a detailed illustration taken either about circle A in FIG. 1 or about circle A in FIG. 2, which depicts the transducer head of the ultrasound transducer, the flat body of the ultrasound transducer, the balloon of the pressure assistance device, and the H-shaped adhesive pad.
Figure 9:
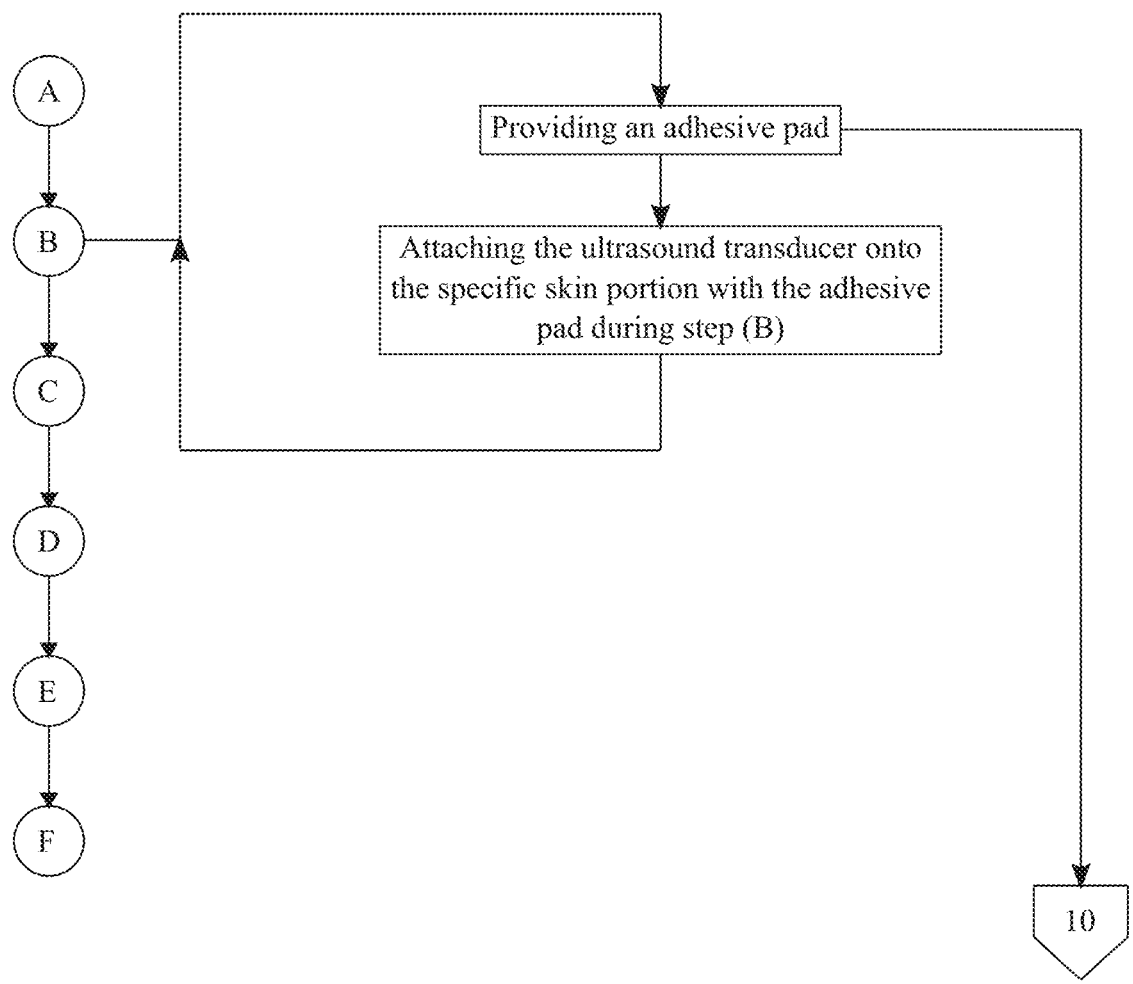
FIG. 9 is a flowchart depicting a subprocess for using an adhesive pad with the ultrasound transducer.

As can be seen in FIGS. 6 and 9, another subprocess for the method of the present invention provides an adhesive pad 13, which is used to hold the ultrasound transducer 1 in place on the specific skin portion 11. Thus, the ultrasound transducer 1 is attached onto the specific skin portion 11 by the adhesive pad 13 during Step B. Consequently, the adhesive pad 13 temporarily secures the ultrasound transducer 1 onto the specific skin portion 11, while using the ultrasound transducer 1, but the adhesive pad 13 allows the ultrasound transducer 1 to be readily detached from the specific skin portion 11 because the adhesive pad 13 does not ever form a permanent bond between the ultrasound transducer 1 and the specific skin portion 11. Moreover, the adhesive pad 13 shown in FIG. 3 preferably includes a first adhesive wing 131, a second adhesive wing 132, a third adhesive wing 133, and a fourth adhesive wing 134, which are arranged into an H-shaped configuration. The first adhesive wing 131 and the second adhesive wing 132 are used to secure a transducer head 3 of the ultrasound transducer 1, while the third adhesive wing 133 and the fourth adhesive wing 134 are used to secure a flat body 2 of the ultrasound transducer 1.

Figure 4:
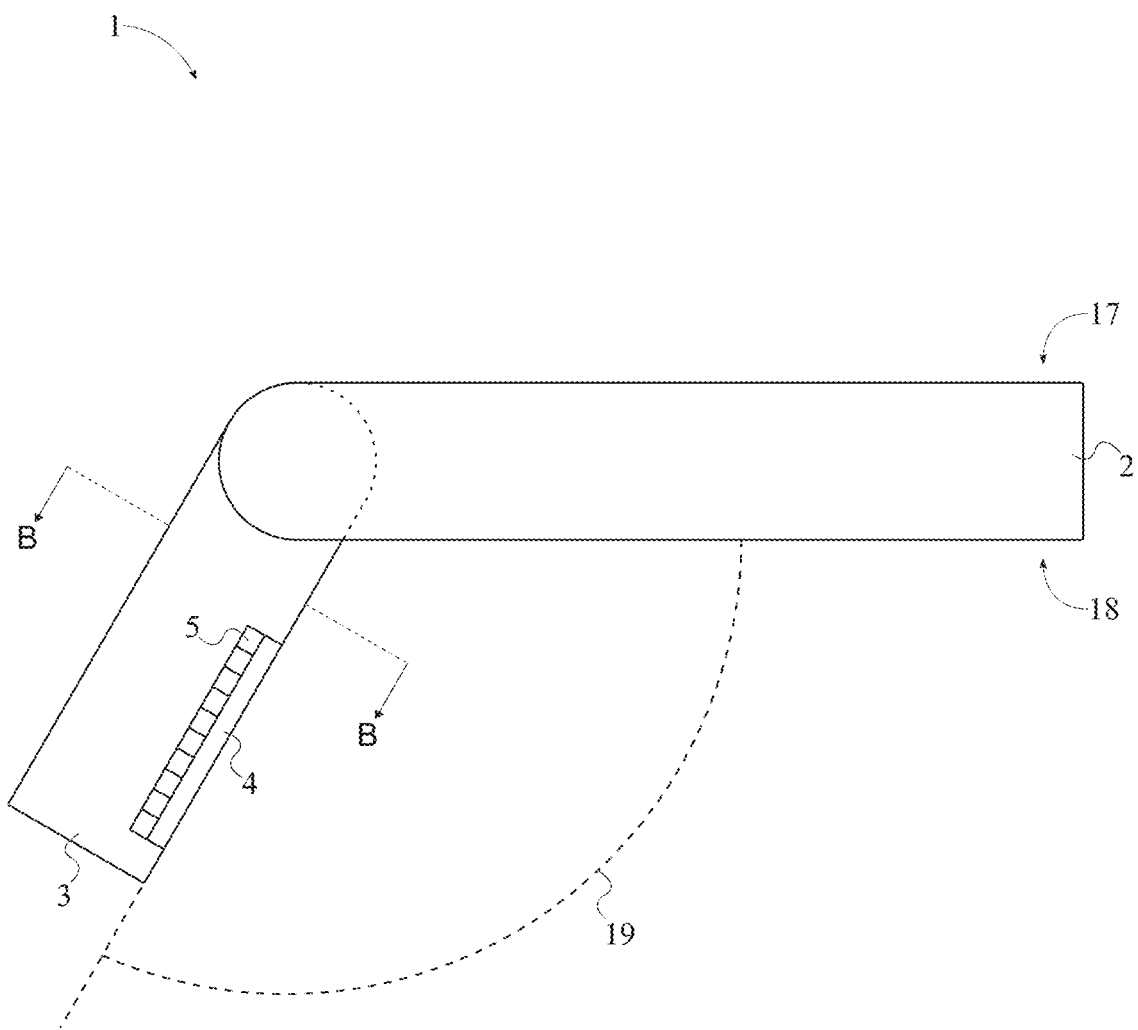
FIG. 4 is an illustration depicting the ultrasound transducer, wherein the transducer head is oriented in relation to the flat body to better accommodate a man or a child.
Figure 5:
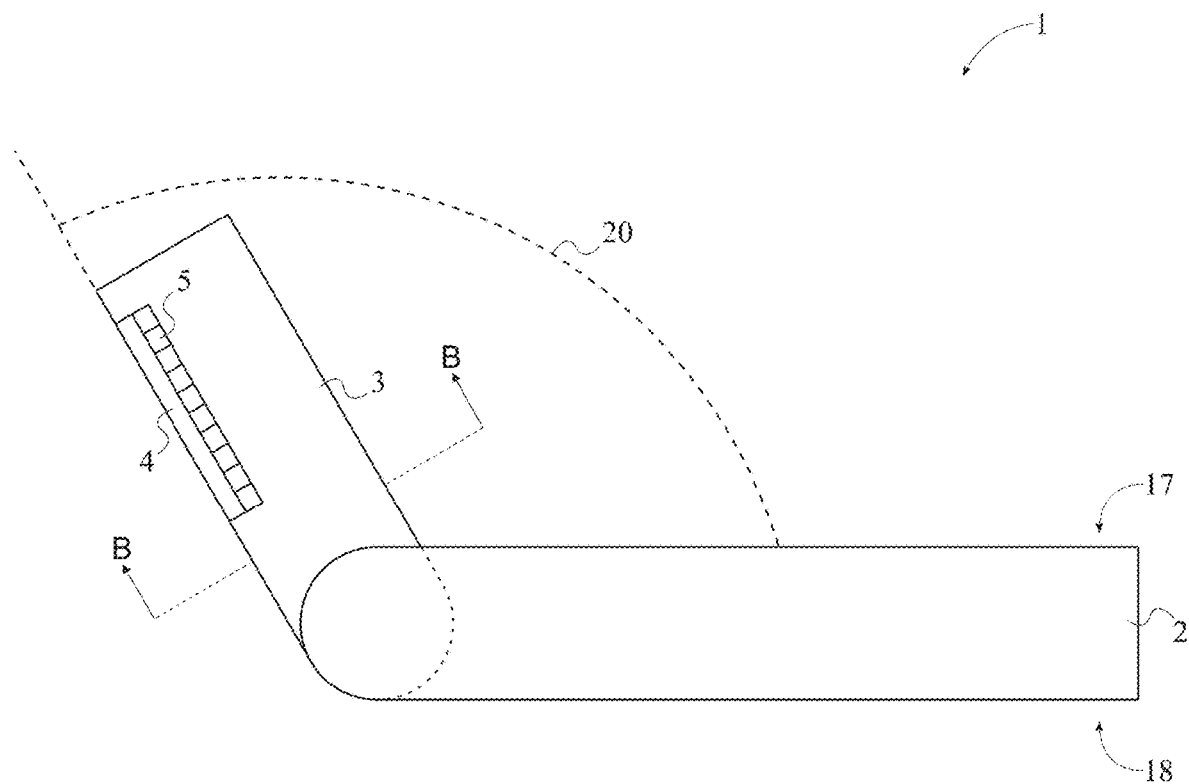
FIG. 5 is another illustration depicting the ultrasound transducer, wherein the transducer head is oriented in relation to the flat body to better accommodate a woman.
Figure 10:
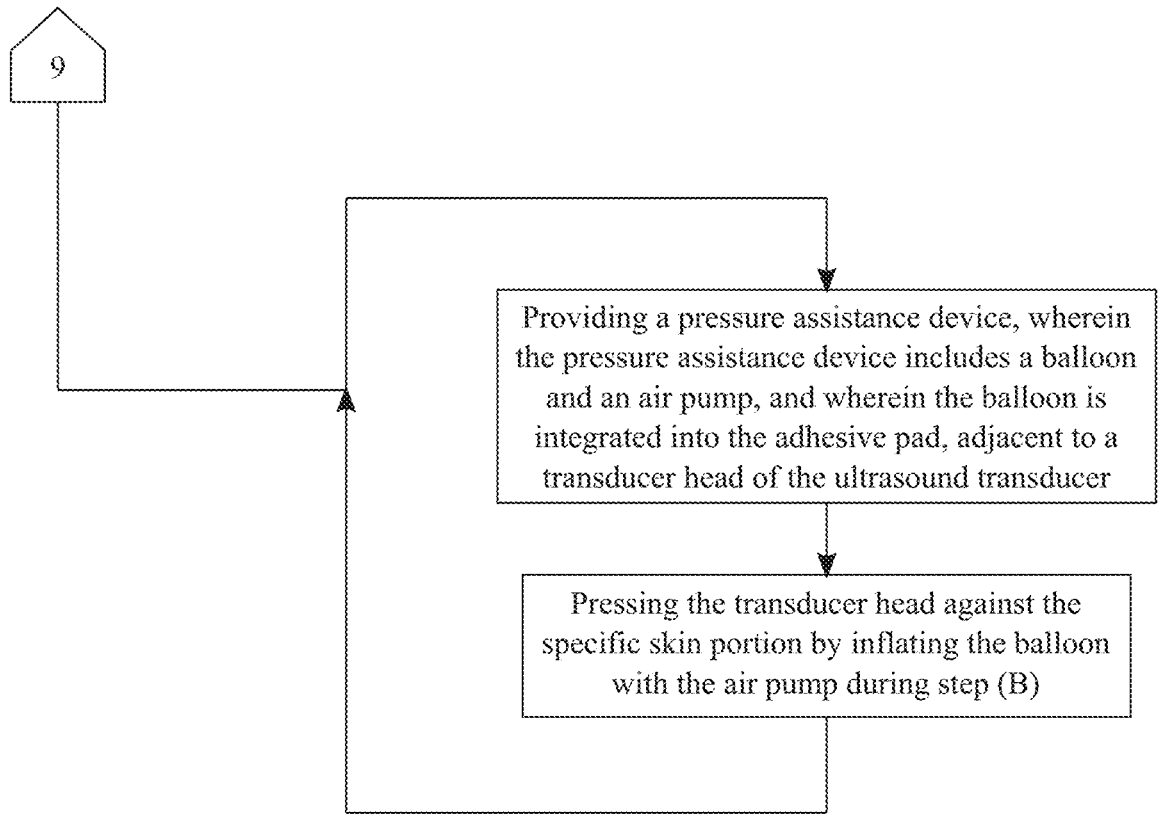
FIG. 10 is a flowchart depicting a subprocess for using a pressure assistance device with the ultrasound transducer.

As can be seen in FIGS. 6 and 10, another subprocess for the method of the present invention provides a pressure assistance device 14, which is also used to hold the ultrasound transducer 1 in place on the specific skin portion 11. The pressure assistance device 14 includes a balloon 15 and an air pump 16. The balloon 15 increases in volumetric size as air is forced into the balloon 15 and decreases in volumetric size as air is released out of the balloon 15. The balloon 15 is integrated into the adhesive pad 13, adjacent to the transducer head 3, opposite to a piezoelectric crystal arrangement 5 of the transducer head 3, which is shown in FIGS. 4 and 5. The air pump 16 is used to force air into the balloon 15 and can be, but is not limited to, a pneumatic compressor or a manual syringe. Thus, the transducer head 3 is pressed against the specific skin portion 11 by inflating the balloon 15 with the air pump 16 during Step B. Consequently, a piezoelectric crystal arrangement 5 and a footprint 4 of the transducer head 3 are held more closely to the specific skin portion 11, even if the patient begins to move around. Similar to the ultrasound gel, the pressure felt by the transducer head 3 against the specific skin portion 11 reduces noise in the continuous echocardiographic data and eventually produces the real-time ultrasound image with a better quality.

In addition, the acquisition of the continuous echocardiographic data could be triggered by a practitioner by directly activating the inflation of the balloon 15 from the bedside monitor 6 via the air pump 16 or by manually injecting air into the balloon 15 by using a syringe. The acquisition of the continuous echocardiographic data could alternatively be self-triggered by a timing scheduled by the practitioner. During this self-triggered process, the balloon 15 will be automatically inflated via the air pump 16 followed by the acquisition of the continuous echocardiographic data. The acquisition duration of the continuous echocardiographic data would be also preset by the practitioner. Moreover, the acquisition of the continuous echocardiographic data would be self-triggered if any abnormality of the vital signs from the beside monitor 6 is outside the preset normal ranges. The acquisition of the continuous echocardiographic data would also automatically stop once the vital signs have normalized.

Figure 11:
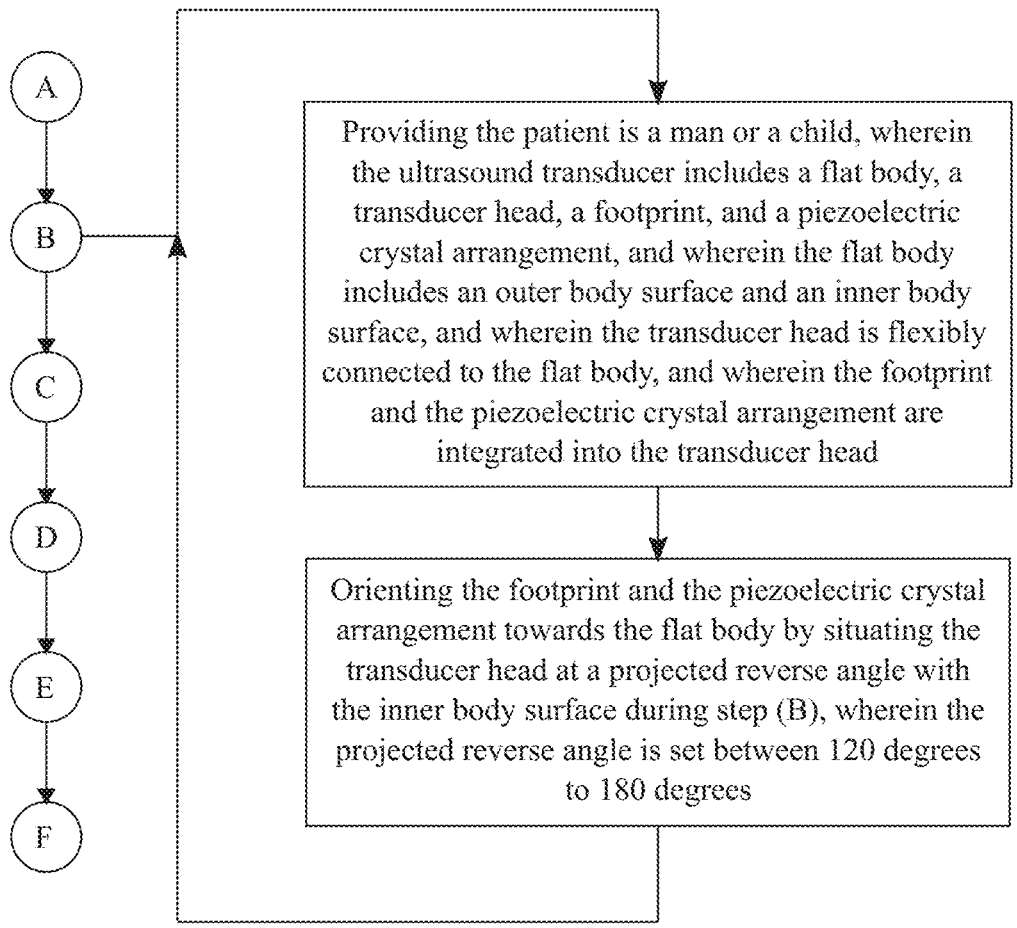
FIG. 11 is a flowchart depicting a subprocess for optimizing the orientation of the transducer head, while the patient using the ultrasound transducer is a man or a child.
Figure 12:
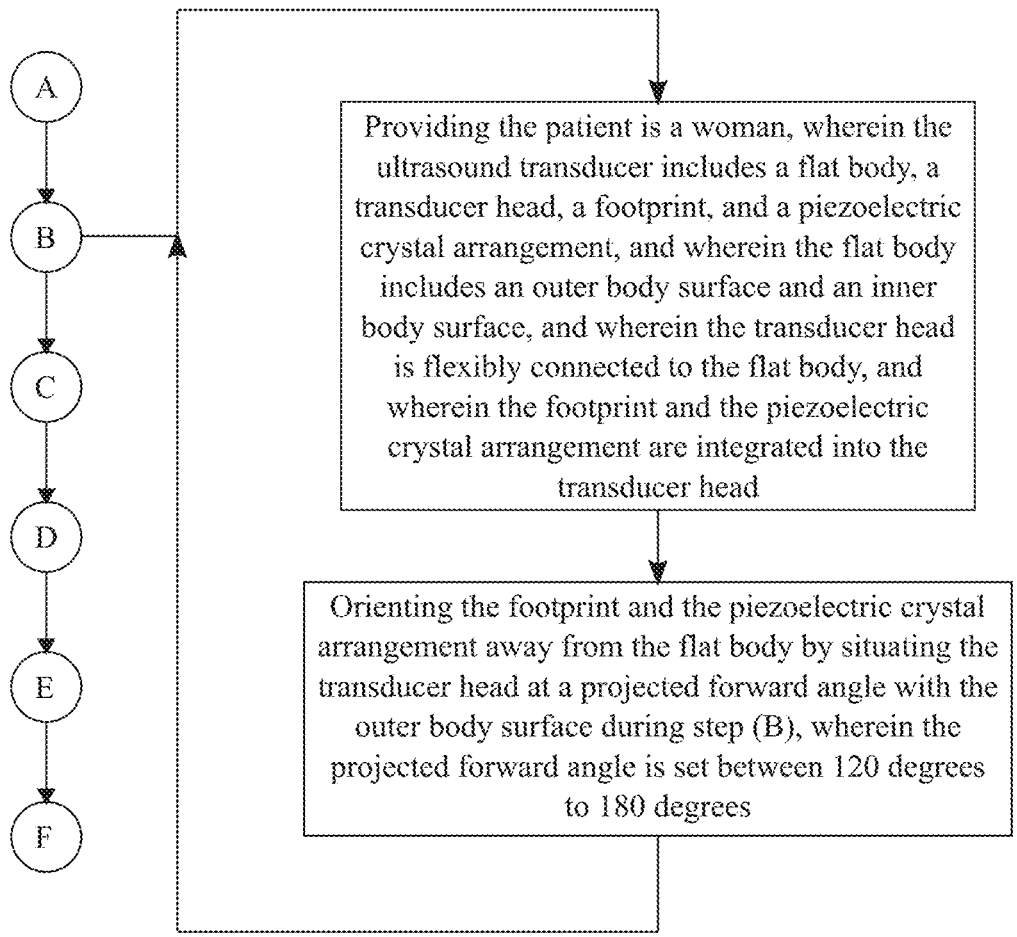
FIG. 12 is a flowchart depicting a subprocess for optimizing the orientation of the transducer head, while the patient using the ultrasound transducer is a woman.

Another subprocess for the method of the present invention provides the ultrasound transducer 1 with a flat body 2, a transducer head 3, a footprint 4, and a piezoelectric crystal arrangement 5, which are shown in FIGS. 4 and 5. The flat body 2 is the main structural portion of the ultrasound transducer 1 and is shaped to be ergonomically positioned against the patient's skin. The flat body 2 includes an outer body surface 17, which is typically facing away from the patient's skin, and an inner body surface 18, which is typically facing towards the patient's skin. The footprint 4 and the piezoelectric crystal arrangement 5 are integrated into the transducer head 3, which allows the transducer head 3 to emit and receive acoustic waves that are used in the ultrasonography of the patient's heart. The transducer head 3 is also flexibly connected to the flat body 2, which allows the transducer head 3 to direct the emission and the reception of those acoustic waves. The flat body 2 is preferably oriented at a projected angle that is set between 120 degrees to 180 degrees from the transducer head 3. The piezoelectric crystal arrangement 5 allows the ultrasound transducer 1 to convert an electrical signal into an acoustic wave and vice versa. The footprint 4 is used to make constant physical contact between the ultrasound transducer 1 and the patient's skin so that the acoustic waves are better able to leave from and return to the ultrasound transducer 1. Moreover, if the patient is a man or a child (FIGS. 4 and 11), then the ultrasound transducer 1 is optimized by situating the transducer head 3 at a projected reverse angle 19 with the inner body surface 18 during Step B, which orients the footprint 4 and the piezoelectric crystal arrangement 5 towards the flat body 2. The projected reverse angle 19 is set between 120 degrees to 180 degrees. Alternatively, if the patient is a woman (FIGS. 5 and 12), then the ultrasound transducer 1 is optimized by situating the transducer head 3 at a projected forward angle 20 with the outer body surface 17 during Step B, which orients the footprint 4 and the piezoelectric crystal arrangement 5 away from the flat body 2. The projected forward angle 20 is set between 120 degrees to 180 degrees.

Figure 13:
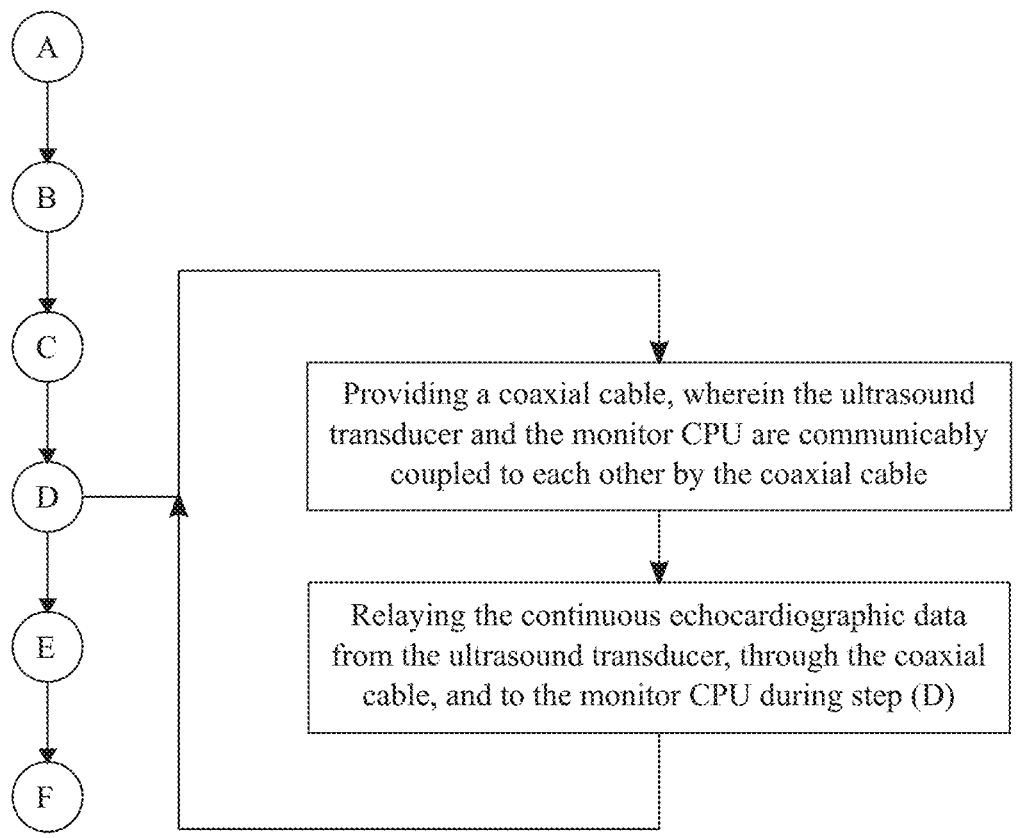
FIG. 13 is a flowchart depicting a subprocess using a coaxial cable with the ultrasound transducer.

As can be seen in FIGS. 1, 2, and 13, another subprocess for the method of the present invention provides a coaxial cable 10, which is used to communicably couple the ultrasound transducer 1 and the monitor CPU 7. Thus, the continuous echocardiographic data is relayed from the ultrasound transducer 1, through the coaxial cable 10, and to the monitor CPU 7 during Step D so that the continuous echocardiographic data is transmitted through a reliable hardwired connection between the ultrasound transducer 1 and the monitor CPU 7.

Figure 14:
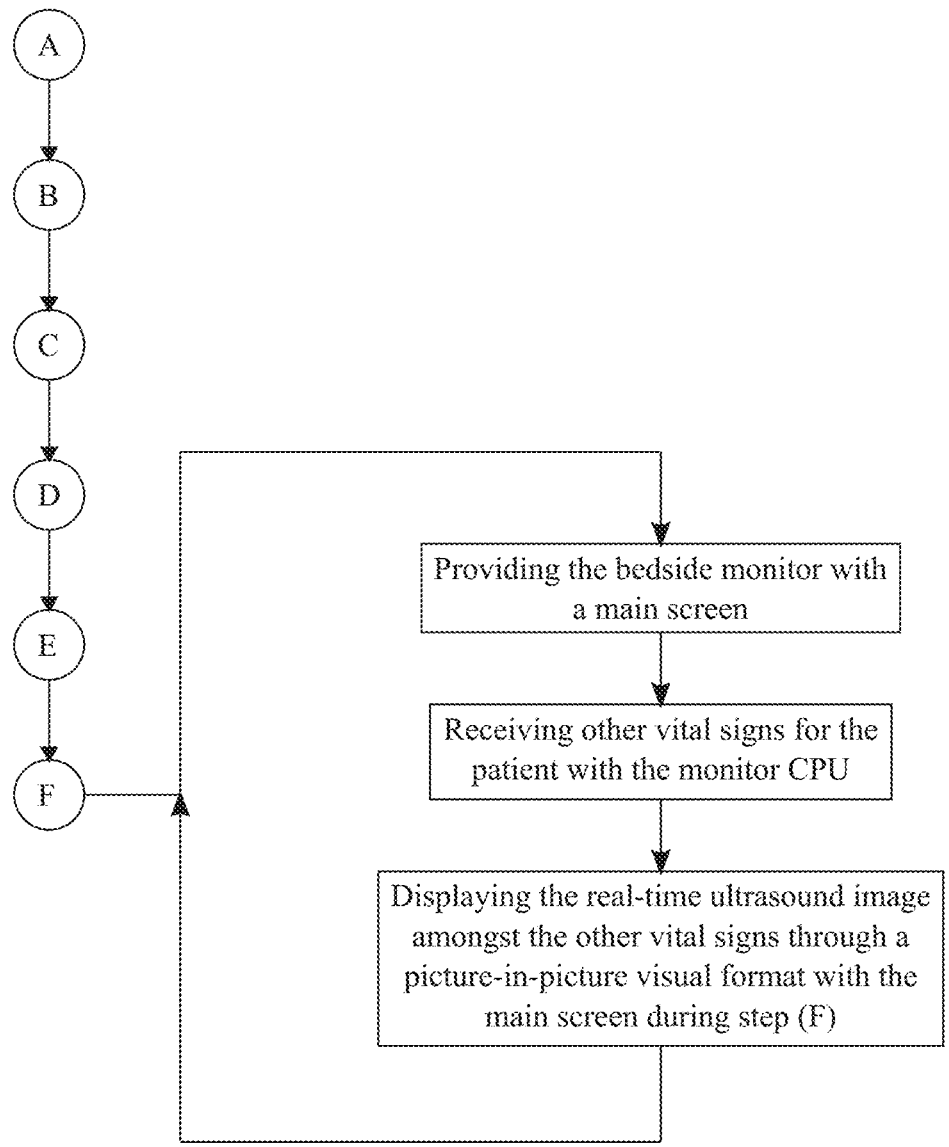
FIG. 14 is a flowchart depicting a subprocess using a main screen of the beside monitor to show the real-time ultrasound image.

As can be seen in FIGS. 1 and 14, another subprocess for the method of the present invention provides the bedside monitor 6 with a main screen 8, which is used to localize the most important medical information about the patient into a primary area of focus for the bedside monitor 6. Thus, the monitor CPU 7 needs to receive other vital signs for the patient, which are sent by other medical sensing devices that have been attached to the patient. Those other vital signs can include, but are not limited to, heart rate, blood pressure, temperature, respiration, and oxygen saturation. Thereafter, the main screen 8 displays the real-time ultrasound image amongst the other vital signs through a picture-in-picture visual format during Step F so that the real-time ultrasound image can be viewed on the primary area of focus for the bedside monitor 6. The picture-in-picture visual format is a smaller viewing window that is superimposed in a larger viewing window, and the smaller viewing window is showing a completely different feed than the larger viewing window. In addition, the real-time ultrasound image is preferably displayed with the smaller viewing window.

Figure 15:
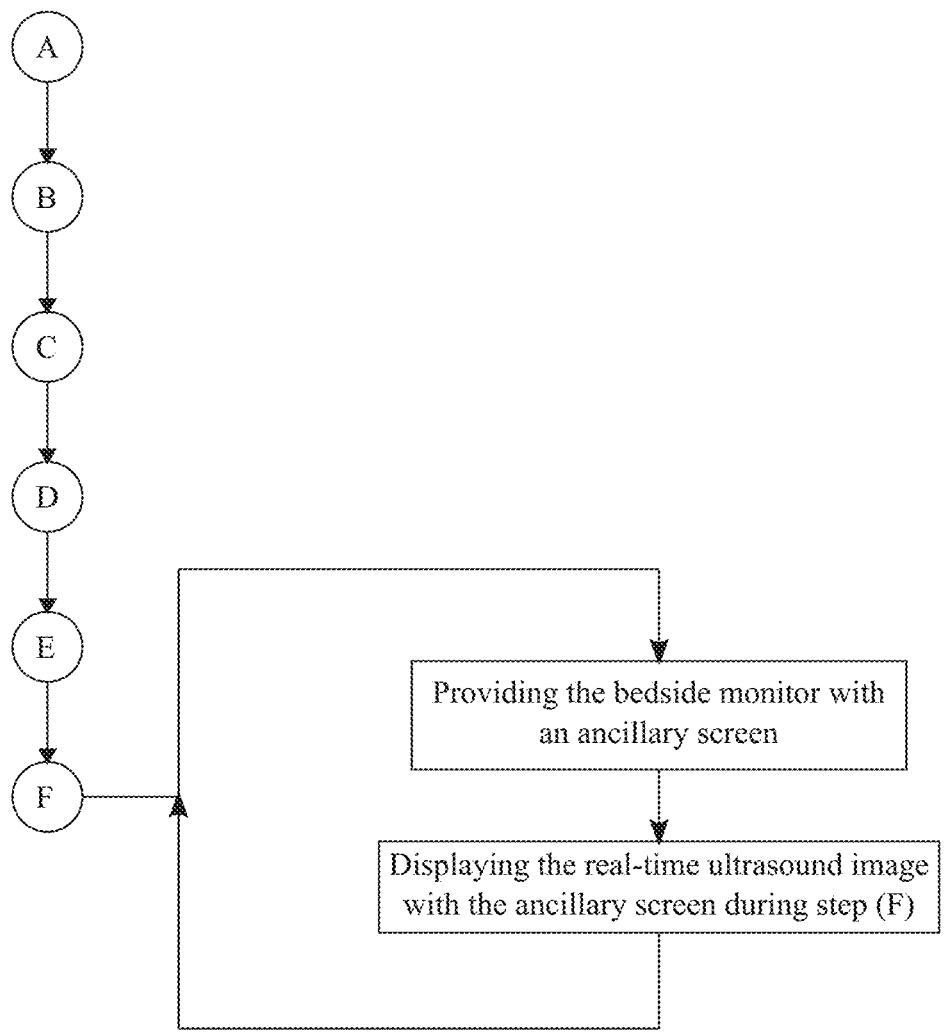
FIG. 15 is a flowchart depicting a subprocess using an ancillary screen of the beside monitor to show the real-time ultrasound image.

As can be seen in FIGS. 2 and 15, another subprocess for the method of the present invention provides the bedside monitor 6 with an ancillary screen 9, which is used to isolate a certain kind of medical information about the patient into a separate area of focus for the bedside monitor 6. Thus, the ancillary screen 9 displays the real-time ultrasound image during Step F so that the real-time ultrasound image can viewed on the separate area of focus for the bedside monitor 6. In some embodiments of the present invention, the ancillary screen 9 can be housed in a separate monitor body that is attached adjacent to the bedside monitor 6 and is used as an accessory to the bedside monitor 6, and that is communicably coupled to the bedside monitor 6 by a data cable.

Figure 16:
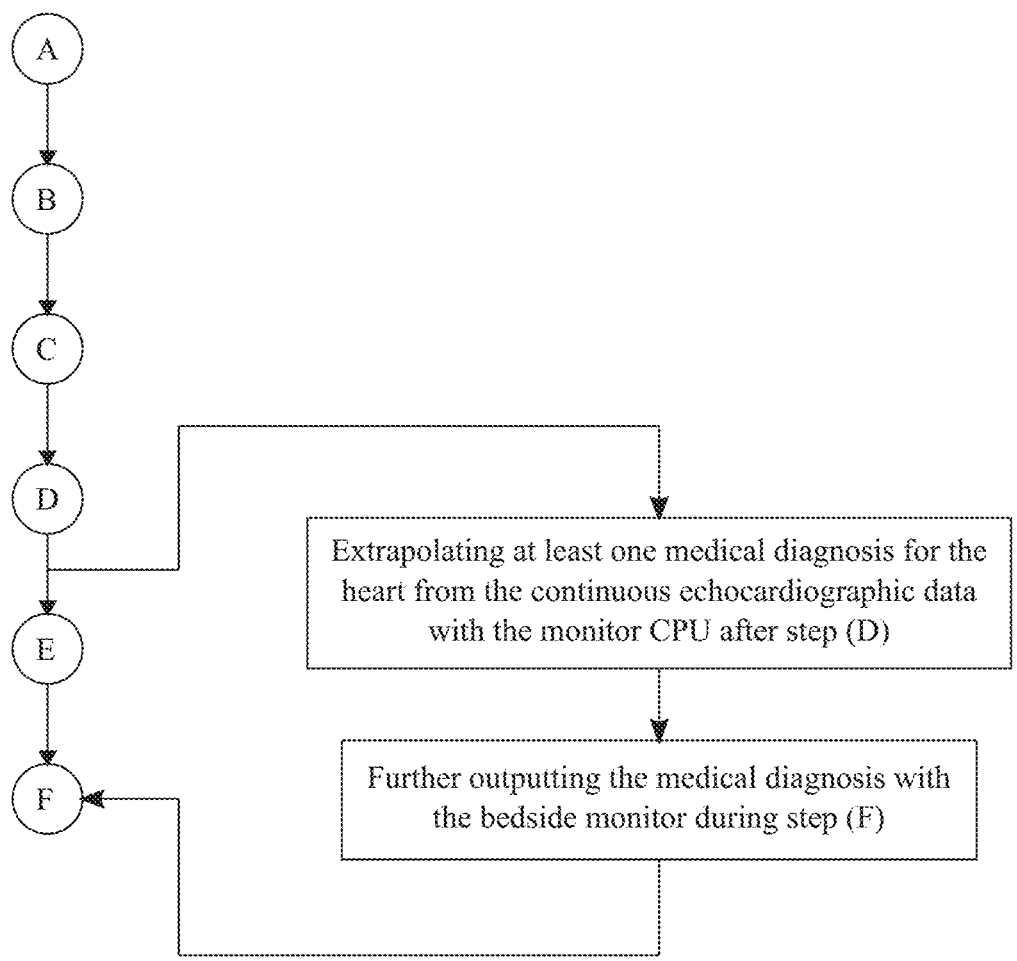
FIG. 16 is a flowchart depicting a subprocess for extrapolating a medical diagnosis for the heart from the continuous echocardiographic data.

As can be seen in FIG. 16, another subprocess for the method of the present invention allows a medical practitioner using the present invention to make at least one medical diagnosis for the patient's heart without the need of a traditional cardiac sonographer and without the need of a conventional ultrasound machine. Thus, the monitor CPU 7 extrapolates at least one medical diagnosis for the patient's heart from the continuous echocardiographic data after Step D so that the monitor CPU 7 is executing some automated calculations based on the continuous echocardiographic data in addition to generating the real-time ultrasound image during Step E. The at least one medical diagnosis can be, but is not limited to, cardiac function, pericardial effusion, intracardiac thrombus/vegetation, intracardiac volume, or combinations thereof. The bedside monitor 6 then outputs the medical diagnosis during Step F so that the medical practitioner can view the medical diagnosis for the patient's heart alongside the real-time ultrasound image of the patient's heart, which provides the medical practitioner with all available information about the patient's heart and allows the medical practitioner to better conduct their medical assessment of the patient's heart.

Figure 17:
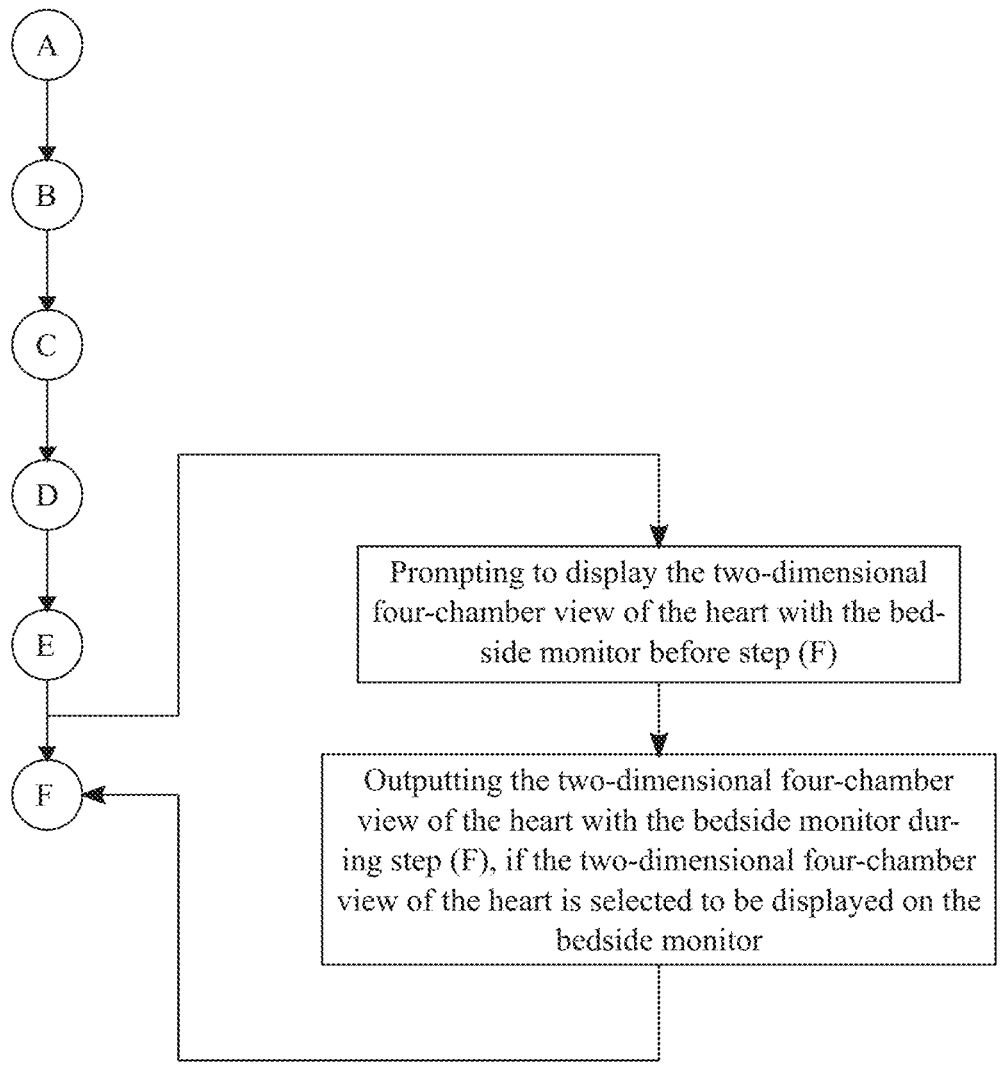
FIG. 17 is a flowchart depicting a subprocess for using a two-dimensional four-chamber view as the real-time ultrasound image.

As can be seen in FIG. 17, another subprocess for the method of the present invention allows a medical practitioner using the present invention to view the real-time ultrasound image of the patient's heart as a two-dimensional four-chamber view. The two-dimensional four-chamber view allows the medical practitioner to calculate and track vital data about the patient's heart (e.g., an ejection fraction, a cardiac volume, etc.). Thus, the beside monitor 6 prompts to display the two-dimensional four-chamber view of the patient's heart before Step F. If the medical practitioner selects the two-dimensional four-chamber view to be displayed on the bedside monitor, the beside monitor would then output the two-dimensional four-chamber view of the patient's heart during Step F. Alternatively, the two-dimensional four-chamber view is the default output for the real-time ultrasound image by the beside monitor during Step F.

Figure 18:
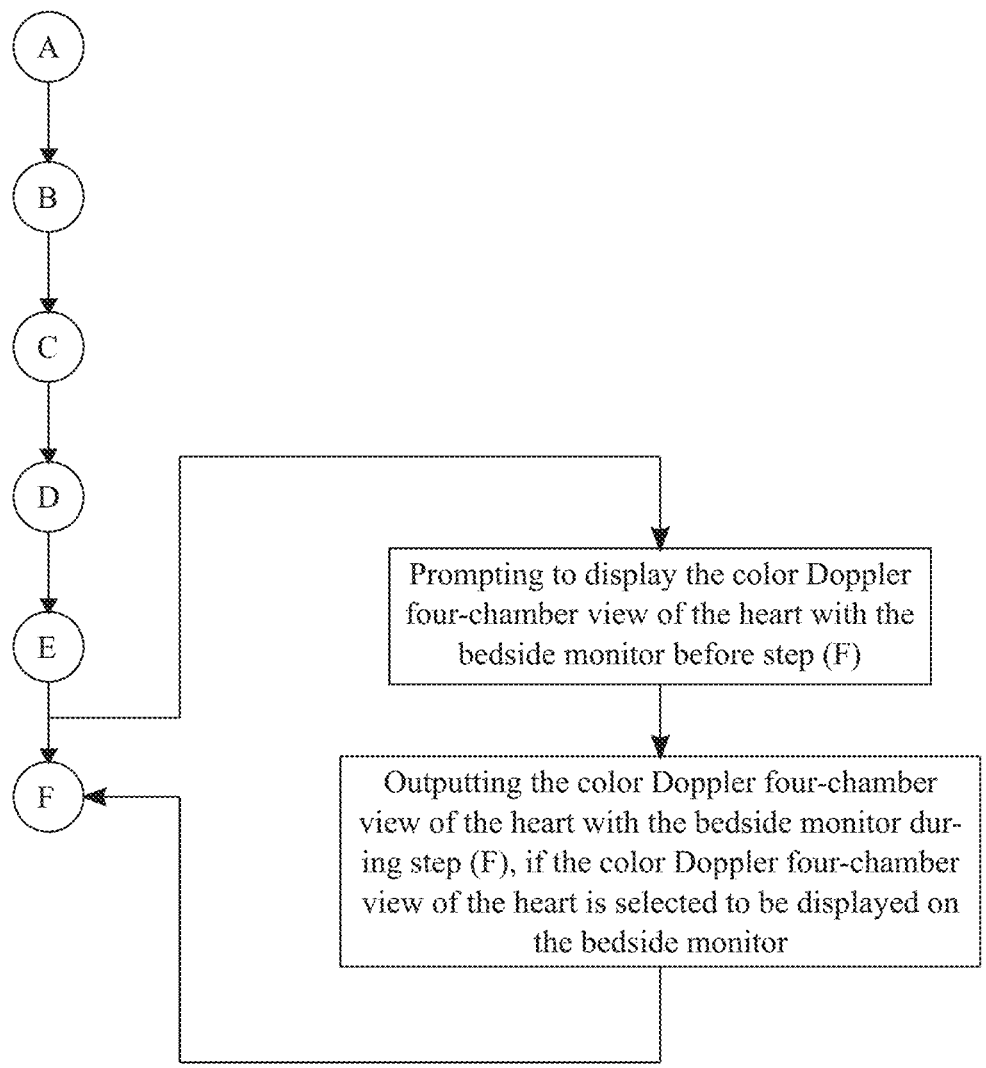
FIG. 18 is a flowchart depicting a subprocess for using a color Doppler four-chamber view as the real-time ultrasound image.

As can be seen in FIG. 18, another subprocess for the method of the present invention allows a medical practitioner using the present invention to view the real-time ultrasound image of the patient's heart as a color Doppler four-chamber view. The color Doppler four-chamber view allows the medical practitioner to view the current directionality of the blood flow towards and away from the ultrasonic transducer. The color Doppler four-chamber view consequently allows the medical practitioner to evaluate and monitor other cardiac conditions such as those conditions involving an obstruction (i.e., stenosis) or leakage (i.e., insufficiency) of the cardiac valves. More specifically, the color Doppler four-chamber view is outputted with a plurality of first flow lines and a plurality of second flow lines. The plurality of first flow lines is a first color and is used to show blood flowing towards the ultrasound transducer 1, while the plurality of second flow lines is in a second color and is used to show blood flowing away from the ultrasound transducer 1. The first color (e.g., a red color) is visually contrasted by the second color (e.g., a blue color) so that the current directionality of the blood flow near the patient's heart can be clearly seen in the color Doppler four-chamber view. Thus, the beside monitor 6 prompts to display the color Doppler four-chamber view of the patient's heart before Step F. This prompting is preferably done with an activation button that is operatively integrated into the bedside monitor 6. If the medical practitioner selects the color Doppler four-chamber view to be displayed on the bedside monitor, the beside monitor would then output the color Doppler four-chamber view of the patient's heart during Step F. Preferably, the color Doppler four-chamber view is graphically superimposed on the two-dimensional four-chamber view.

Figure 19:
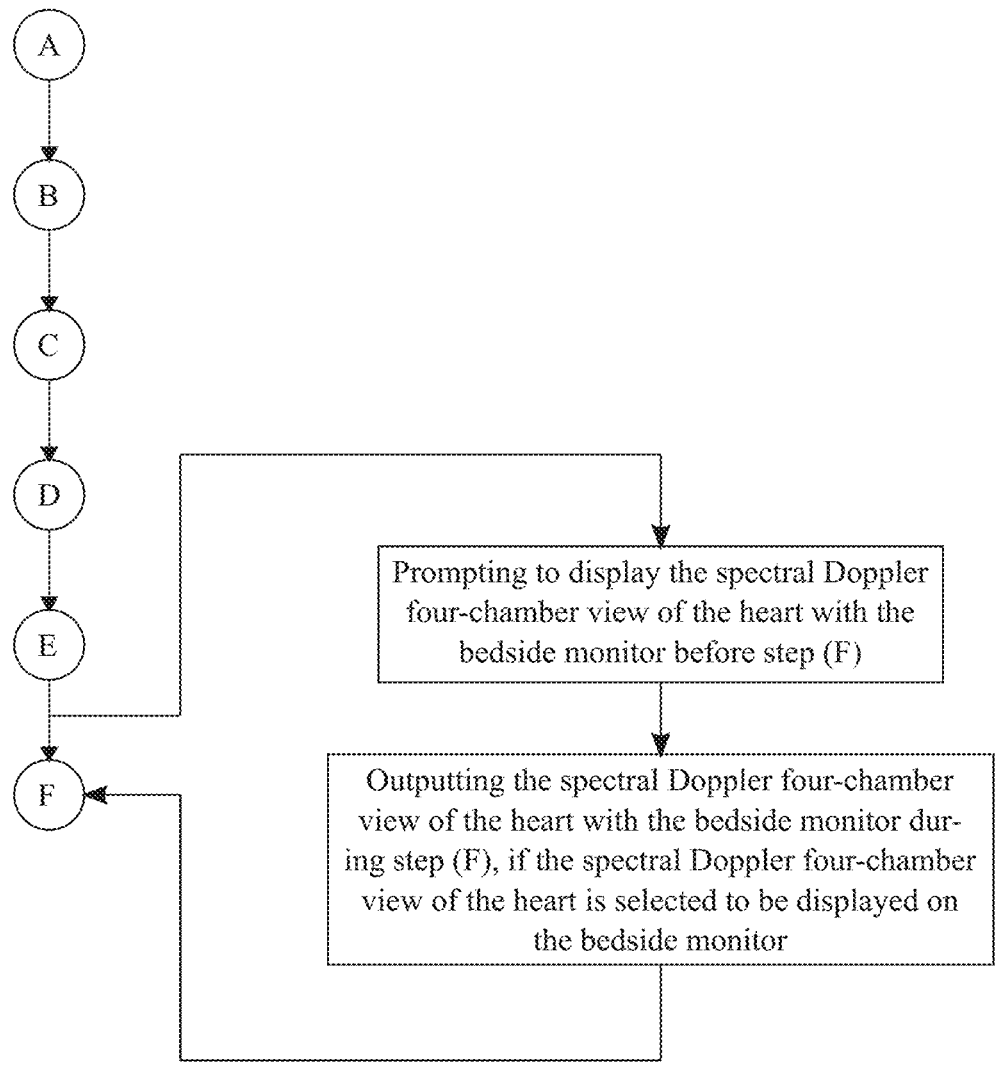
FIG. 19 is a flowchart depicting a subprocess for using a spectral Doppler four-chamber view as the real-time ultrasound image.

As can be seen in FIG. 19, another subprocess for the method of the present invention allows a medical practitioner using the present invention to view the real-time ultrasound image of the patient's heart as a spectral Doppler four-chamber view. The spectral Doppler four-chamber view allows the medical practitioner to view the directionality over time of the blood flow towards and away from the ultrasonic transducer. In those patients with stenosis or insufficiency of the cardiac valves, the spectral Doppler four-chamber view can be used with a sample volume to calculate the velocity of the blood flow in either direction by showing a graphical representation of the blood flow of the region of interest over time. Thus, the beside monitor 6 prompts to display the spectral Doppler four-chamber view of the patient's heart before Step F. This prompting is preferably done with another activation button that is operatively integrated into the bedside monitor 6. If the medical practitioner selects the spectral Doppler four-chamber view to be displayed on the bedside monitor, the beside monitor would then output the spectral Doppler four-chamber view of the patient's heart during Step F. Preferably, the spectral Doppler four-chamber view is graphically adjacent to the color Doppler four-chamber view that is graphically superimposed on the two-dimensional four-chamber view.

Figure 20:
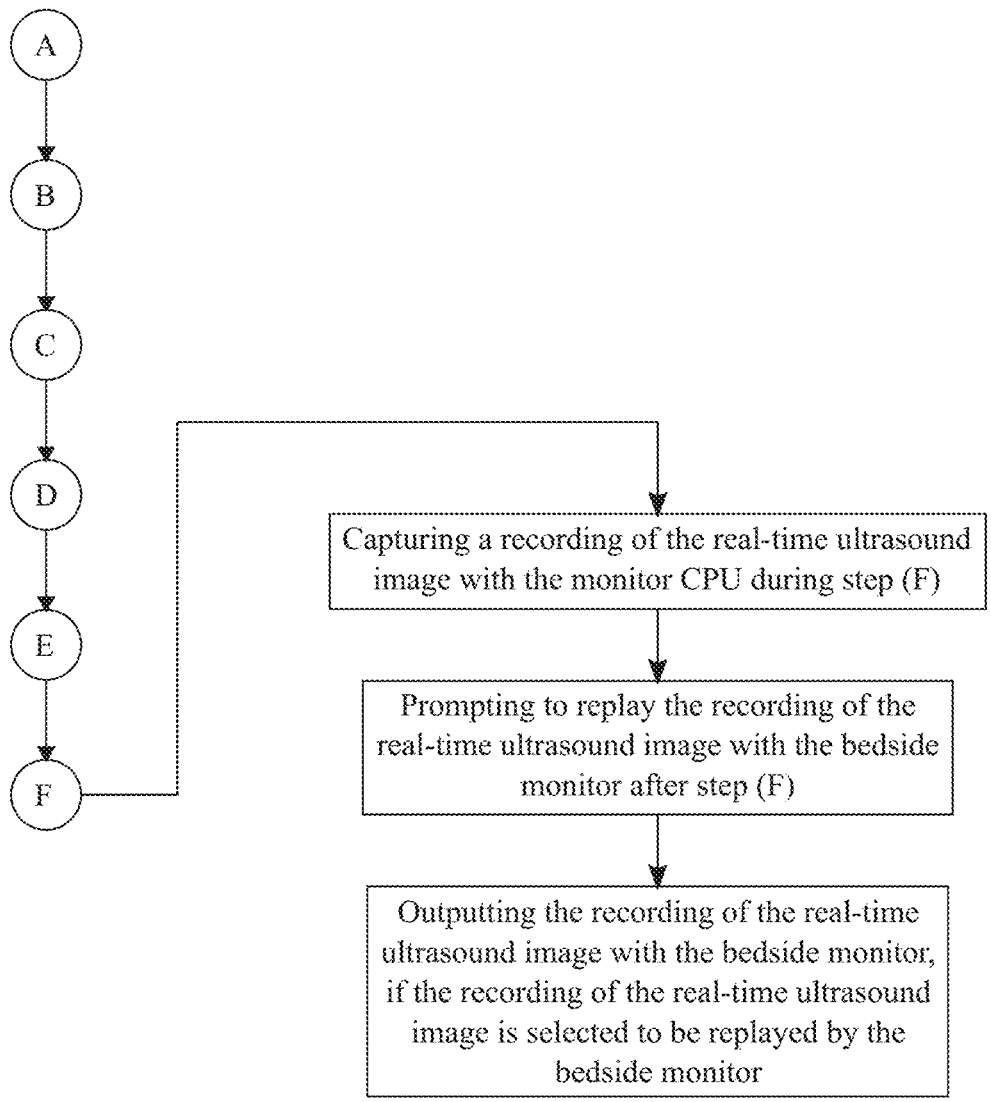
FIG. 20 is a flowchart depicting a subprocess for using a playback feature for the real-time ultrasound image.

As can be seen in FIG. 20, another subprocess for the method of the present invention allows a medical practitioner using the present invention to playback an already-played portion of the real-time ultrasound image. This subprocess begins by capturing a recording of the real-time ultrasound image with the monitor CPU 7 during Step F, which allows any already-played portion of the real-time ultrasound image to be readily viewable to the medical practitioner. Consequently, the bedside monitor 6 prompts to replay the recording of the real-time ultrasound image after Step F so that the medical practitioner has the option to pay closer attention to or to re-watch some specific piece of visual information in the real-time ultrasound image. If the recording of the real-time ultrasound image is selected to be replayed by the bedside monitor 6, then this subprocess concludes by outputting the recording of the real-time ultrasound image with the bedside monitor 6. This results in the medical practitioner having a better understanding of some specific piece of visual information in the real-time ultrasound image and subsequently conducting a better medical assessment of the patient's heart.

Figure 21:
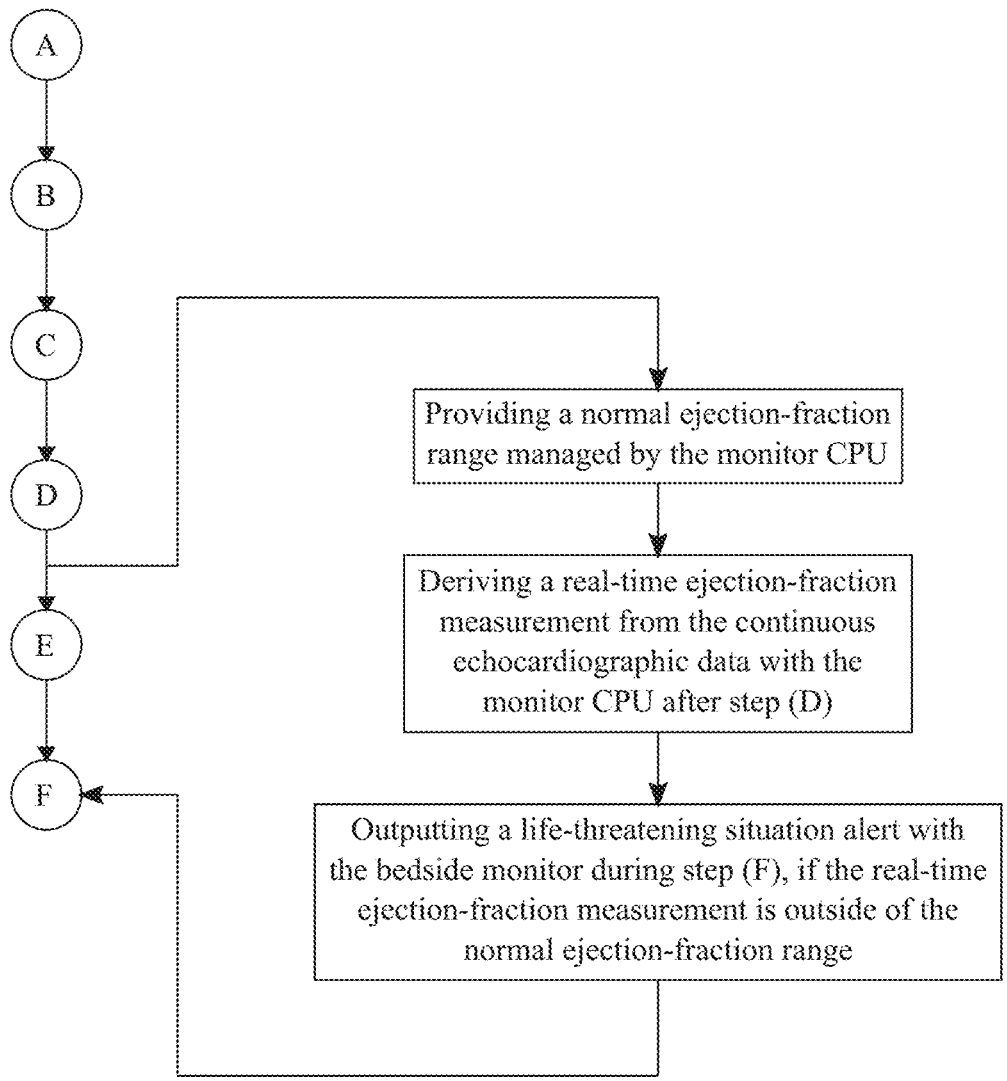
FIG. 21 is a flowchart depicting a subprocess for alerting based on the ejection-fraction of the patient's heart.

As can be seen in FIG. 21, another subprocess for the method of the present invention provides a normal ejection-fraction range, which is a metric that quantifies the health of the patient's heart. More specifically, the normal ejection-fraction range is a percentage range for a normal amount of blood that should be pumped out of the left ventricle. The normal ejection-fraction range is managed by the monitor CPU 7 so that the normal ejection-fraction range can be readily referenced by the monitor CPU 7. In contrast, the monitor CPU 7 derives a real-time ejection-fraction measurement from the continuous echocardiographic data after Step D. The real-time ejection-fraction measurement is a real-time percentage of an actual amount of blood that is being pumped out of the left ventricle. The real-time ejection-fraction measurement is preferably calculated by auto-tracing of the endocardial borders of the left ventricle, which would be enabled by a medical practitioner at any desired time or set time period. Moreover, if the real-time ejection-fraction measurement is inside of the normal ejection-fraction range, then the patient's heart is normally functioning. However, if the real-time ejection-fraction measurement is outside of the normal ejection-fraction range, then the bedside monitor 6 outputs a life-threatening situation alert during Step F, which should immediately grab the attention of a medical practitioner. The most likely scenario would be that the life-threatening situation alert is outputted with the bedside monitor 6 because the real-time ejection-fraction measure is less than a lower end of the normal ejection-fraction range.

Figure 22:
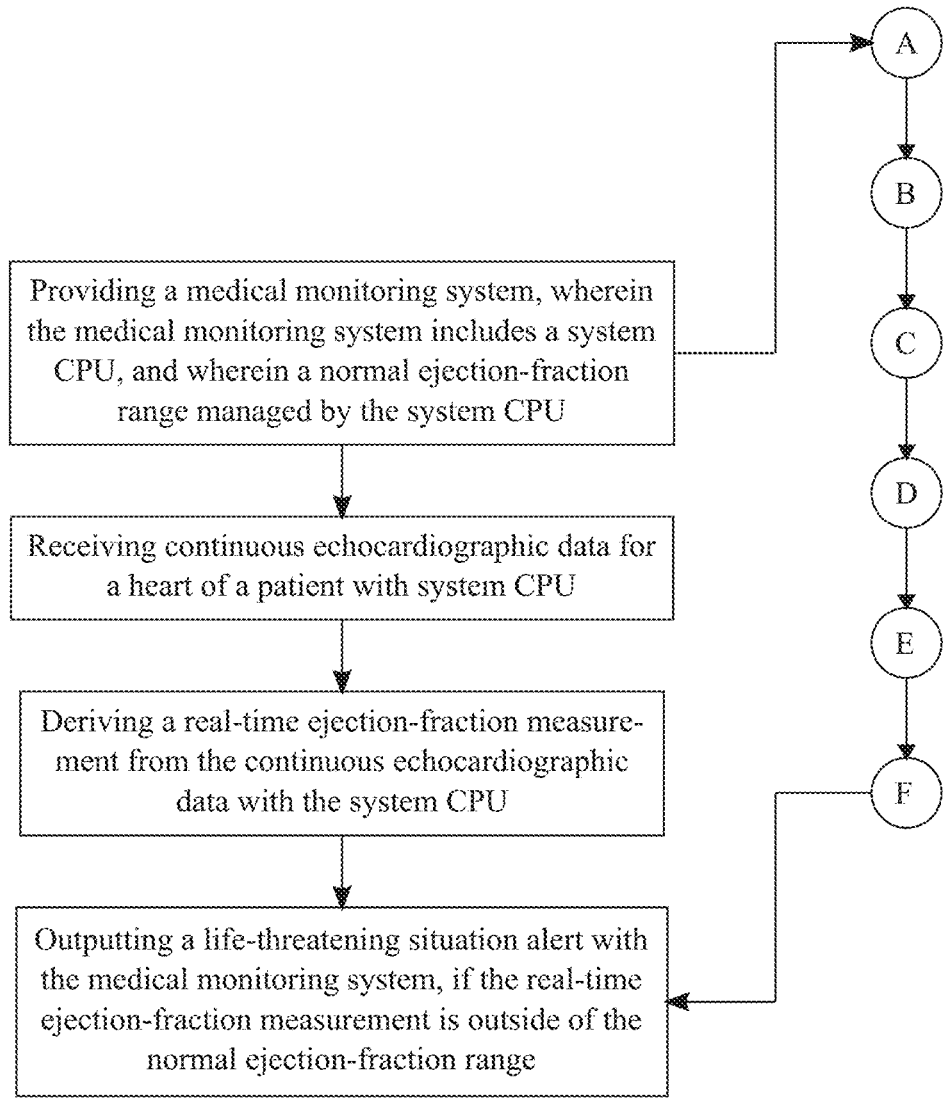
FIG. 22 is a flowchart depicting an overall process for the method of monitoring a life-threating medical situation based on an ejection-fraction measurement.

As can be seen in FIG. 22, some embodiments of the present invention are focused on a system and a method of monitoring a life-threating medical situation based on an ejection-fraction measurement. The system of these embodiments is provided with a medical monitoring system that is used to track at least one vital of a patient. The medical monitoring system includes a system CPU, which allows the medical monitoring system to manage and process electronic commands and data for the medical monitoring system. The system CPU for these embodiments manages the normal ejection-fraction range. An overall process for the method of these embodiments begins by receiving the continuous echocardiographic data for a patient's heart with system CPU, and the continuous echocardiographic data in these embodiments can be collected by an ultrasonic transducer, a transthoracic echocardiogram, a transesophageal echocardiogram, an intracardiac echocardiography, or any other kind of medical imaging. The overall process of these embodiments continues by deriving a real-time ejection-fraction measurement from the continuous echocardiographic data with the system CPU so that the real-time ejection-fraction measurement is readily available to assess the health of the patient's heart. The overall process of these embodiments concludes by outputting a life-threatening situation alert with the medical monitoring system, if the real-time ejection-fraction measurement is outside of the normal ejection-fraction range. The most likely scenario would again be that the life-threatening situation alert is outputted with the medical monitoring system because the real-time ejection-fraction measurement is less than a lower end of the normal ejection-fraction range. In order to relate these embodiments to rest of the present invention, the medical monitoring system can be, but is not limited to, a combination of the ultrasound transducer 1 and the bedside monitor 6, and the system CPU is a monitor CPU 7 of the bedside monitor 6.

The present invention is helpful to a medical practitioner for a variety of procedures while assessing the health of the patient's heart without the need of a cardiac sonographer or the need of a conventional portable ultrasound machine. One example is executing Step B through Step F during a catheter interventional procedure, which treats or repairs an ailment with the patient's heart through a heart catheterization. Another example is executing Step B through Step F during a cannula placement procedure for extracorporeal membrane oxygenation, which attaches a cannula to the patient's heart to better oxygenate the blood around the patient's heart. Another example is executing Step B through Step F during a cannula removal procedure for extracorporeal membrane oxygenation, which detaches a cannula from the patient's heart after the cannula is done oxygenating the blood around the patient's heart. Another example is executing Step B through Step F during a pericardiocentesis procedure, which drains fluid around the patient's heart by inserting a needle into the pericardial space of the patient's heart.

Figure 23:
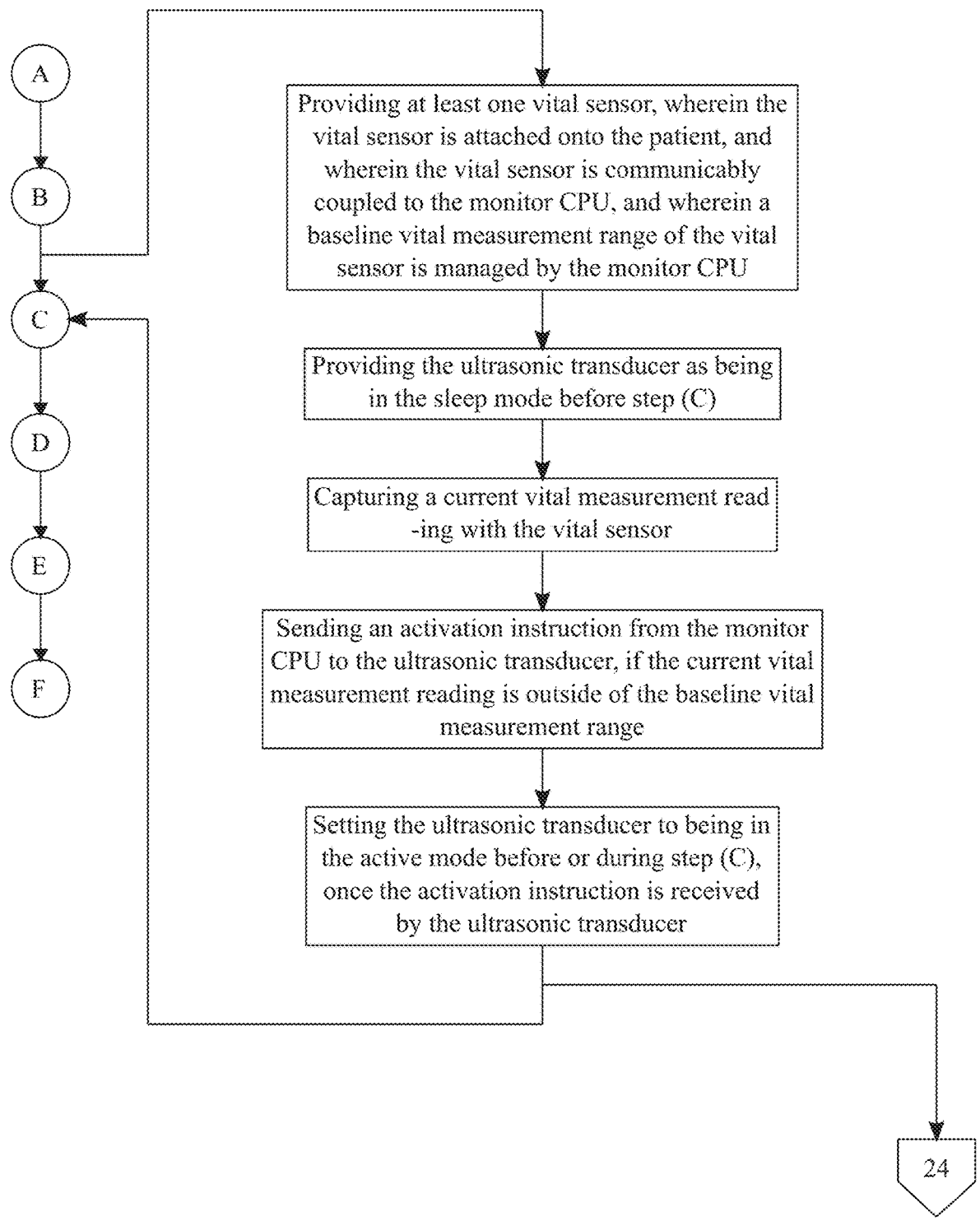
FIG. 23 is a flowchart depicting a subprocess for transitioning the ultrasound transducer from a sleep mode to an active mode based on a patient's vital signs.
Figure 24:
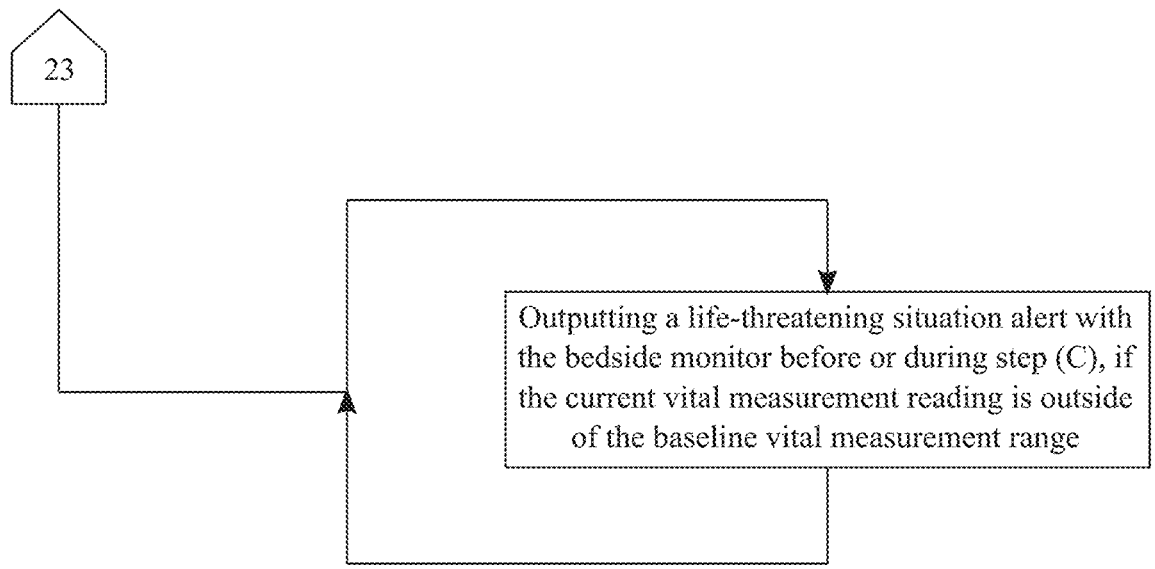
FIG. 24 is a flowchart depicting a subprocess for alerting based on a patient's vital signs.

The present invention may allow the ultrasonic transducer 1 to transition from its sleep mode to its active mode through one of three triggering subprocesses. As can be seen in FIGS. 1, 2, and 23, the first triggering subprocess transitions the ultrasonic transducer 1 from its sleep mode to its active mode with at least one vital sensor 17, which is attached onto the patient and is consequently used to measure vital signs from the patient. The at least one vital sensor 17 can be, but is not limited to, an electrocardiography (ECG) sensor, an oxygen saturation sensor, a blood pressure sensor, or combinations thereof. Moreover, a baseline vital measurement range of the vital sensor 17 is managed by the monitor CPU 7. The baseline vital measurement range defines a normal range of measurements that can be taken by the vital sensor 17. For example, the baseline vital measurement range of an oxygen saturation is the normal range of oxygen saturation that should be detected within the patient. The vital sensor 17 is also communicably coupled to the monitor CPU 7. The vital sensor 17 is preferably in wireless communication with the monitor CPU 7 through a personal area network (e.g., Bluetooth). In addition, if the ultrasonic transducer 1 is in its sleep mode before Step C, the first triggering process begins by capturing a current vital measurement reading with the vital sensor 17 so that the monitor CPU 7 is able to continuously needs to monitor at least one vital sign of the patient. The first triggering subprocess continues by sending an activation instruction from the monitor CPU 7 to the ultrasonic transducer 1, if the current vital measurement reading is outside of the baseline vital measurement range, so that the monitor CPU 7 is able to "wake up" the ultrasonic transducer 1. For example, this would occur if the patient was undergoing cardiac arrest. The first triggering process concludes by setting the ultrasonic transducer 1 as being in its active mode before or during Step C, once the activation instruction is received by the ultrasonic transducer 1, so that the ultrasonic transducer 1 is able to capture echocardiographic data while the patient is experiencing an abnormal vital sign. As can be seen in FIG. 24, the bedside monitor 6 may also output a life-threatening situation alert before or during Step C, if the current vital measurement reading is outside of the baseline vital measurement range, thereby alerting a medical practitioner of an abnormal vital sign of the patient. After the first triggering process is complete, the ultrasonic transducer 1 resets to being in its sleep mode, if the current vital measurement reading is again within the baseline vital measurement range. For example, this would occur if the patient was relieved from cardiac arrest.

Figure 25:
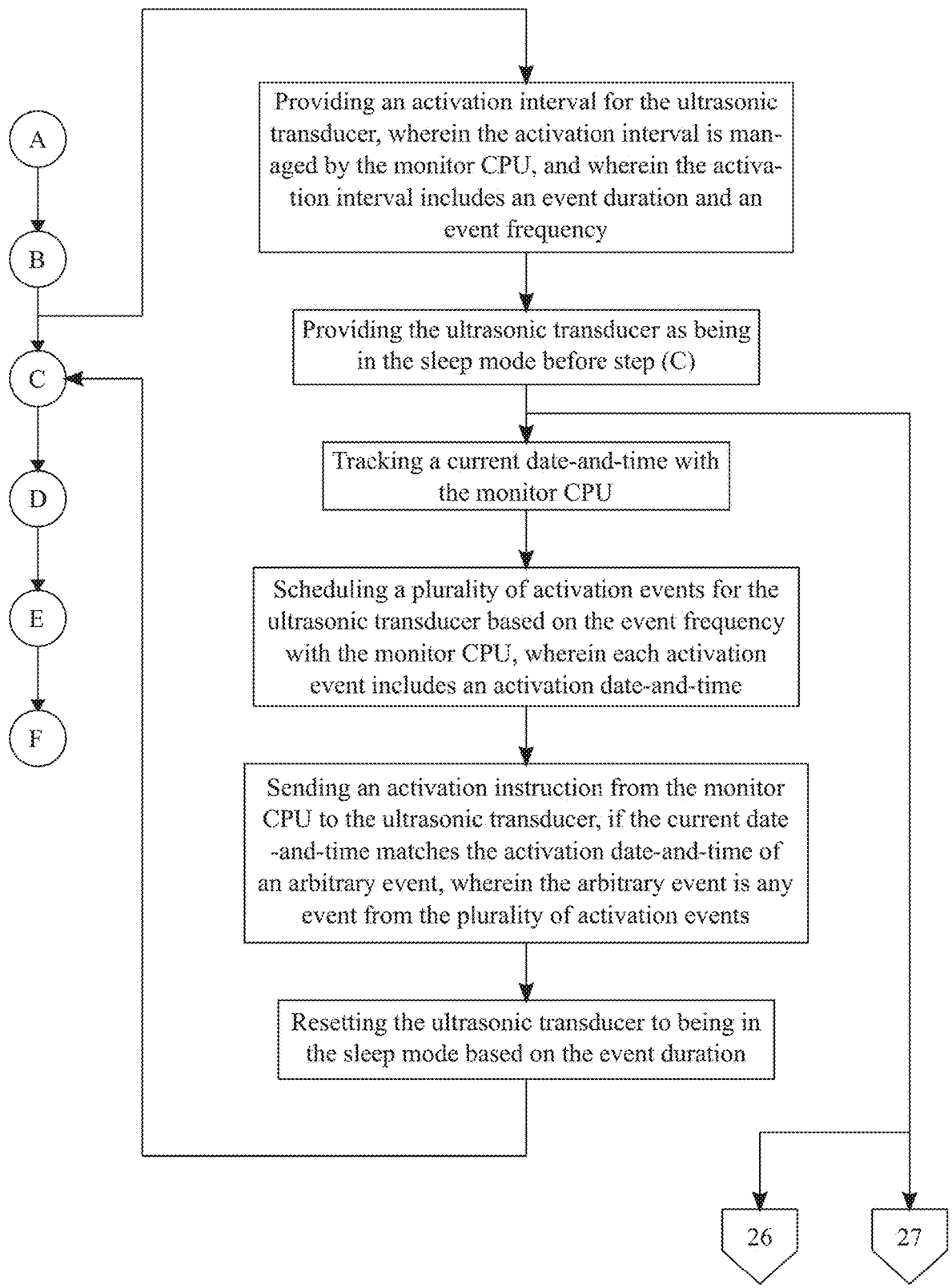
FIG. 25 is a flowchart depicting a subprocess for transitioning the ultrasound transducer from a sleep mode to an active mode based on an automated activation interval.

As can be seen in FIG. 25, the second triggering subprocess transitions the ultrasonic transducer 1 from its sleep mode to its active mode with an activation interval for the ultrasonic transducer 1, wherein the activation interval is managed by the monitor CPU 7. The activation interval is a regular interval that the monitor CPU 7 automatically "wakes up" the ultrasonic transducer 1 in order to capture echocardiographic data. For example, the activation interval can be set to three times a day (i.e., an event frequency) that the ultrasonic transducer 1 "wakes up" and captures echocardiographic data for 5 minutes (i.e., an event duration). In addition, if the ultrasonic transducer 1 is in its sleep mode before Step C, the second triggering process begins by tracking a current date-and-time with the monitor CPU 7 and by scheduling a plurality of activation events for the ultrasonic transducer 1 based on an event frequency of the activation interval with the monitor CPU 7. Each activation event is a scheduled event based on the activation interval to "wake up" the ultrasonic transducer 1 and to capture a certain amount of echocardiographic data before the ultrasonic transducer 1 "falls asleep" again. Each activation event also has a specific activation date-and-time. The second triggering subprocess continues by sending an activation instruction from the monitor CPU 7 to the ultrasonic transducer 1, if the current date-and-time matches the activation date-and-time of an arbitrary event, so that the monitor CPU 7 is able to "wake up" the ultrasonic transducer 1. The arbitrary event can be any event from the plurality of activation events. The second triggering process continues by setting the ultrasonic transducer 1 as being in its active mode before or during Step C, once the activation instruction is received by the ultrasonic transducer 1, so that the ultrasonic transducer 1 is able to capture echocardiographic data at a predetermined date-and-time. The second triggering process concludes by resetting the ultrasonic transducer 1 to being in the sleep mode based on an event duration of activation interval so that the ultrasonic transducer 1 is only in its active mode for brief moments at specific times of a day.

Figure 26:
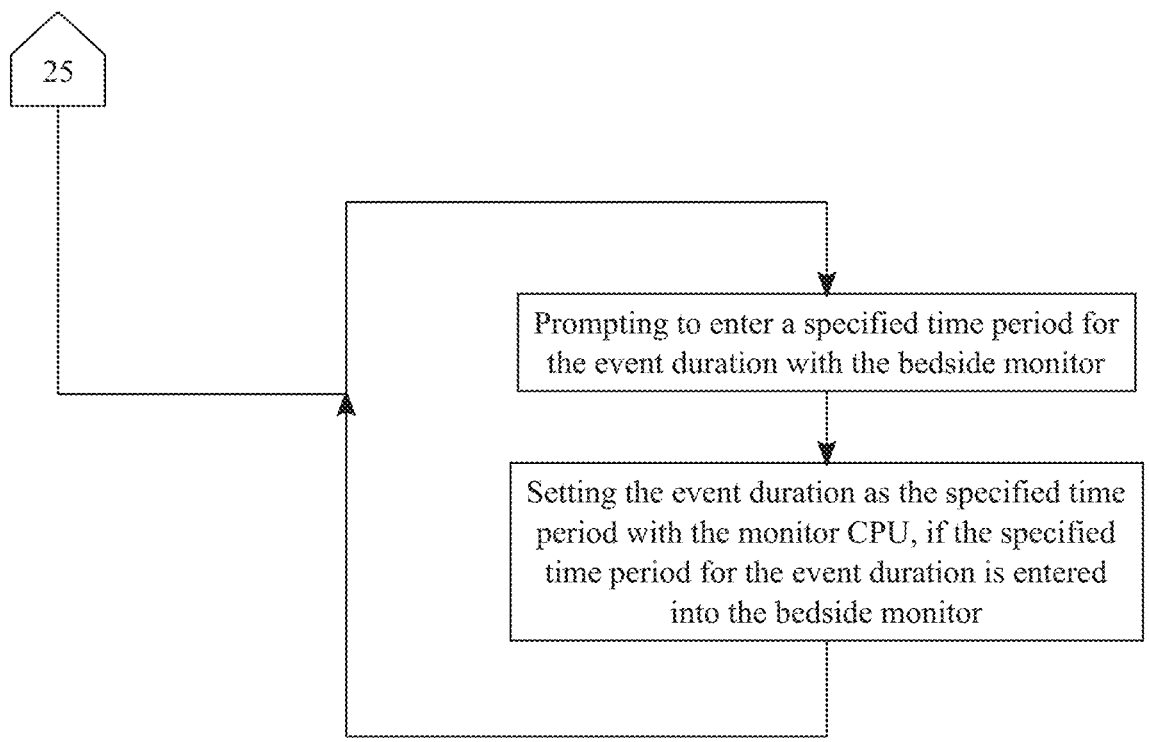
FIG. 26 is a flowchart depicting a subprocess for setting an event duration of the automated activation interval.
Figure 27:
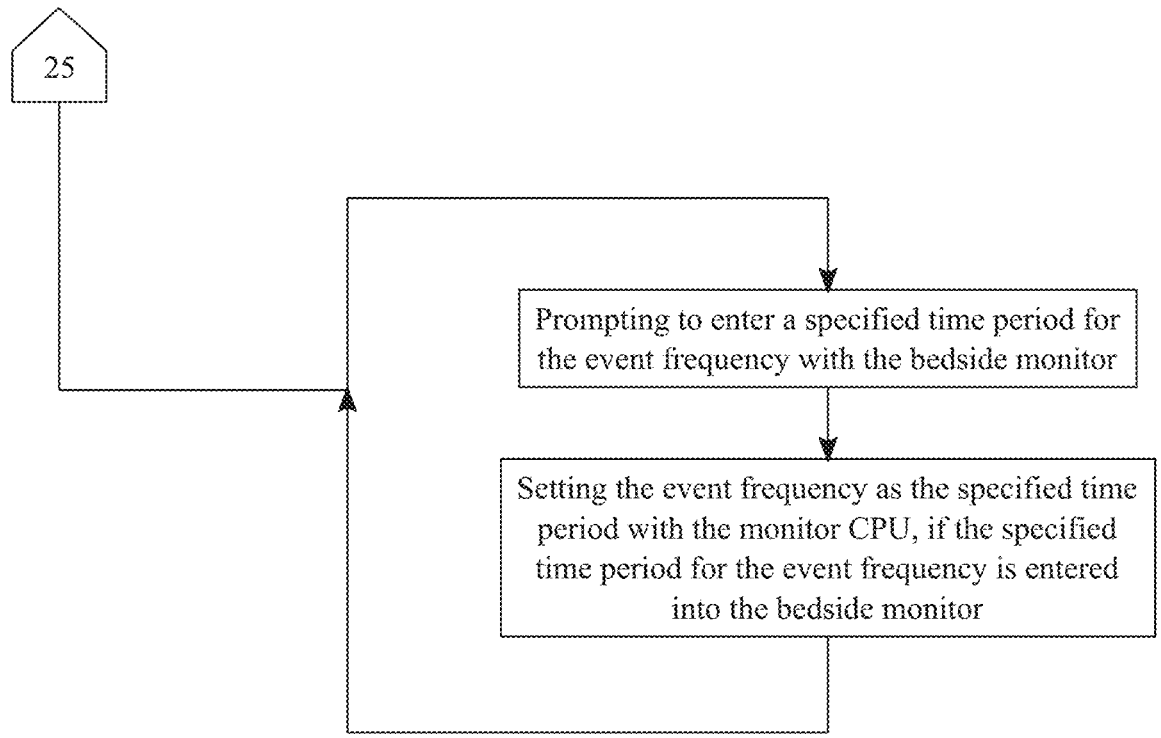
FIG. 27 is a flowchart depicting a subprocess for setting an event frequency of the automated activation interval.

The event duration and the event frequency of the activation interval are used to schedule the plurality of activation events. The event duration is the length of time that the ultrasonic transducer 1 captures echocardiography data during an activation event. As can be seen in FIG. 26, in order to set the event duration, the bedside monitor 6 prompts to enter a specified time period for the event duration. If the specified time period for the event duration is entered into the bedside monitor 6, the monitor CPU 7 then sets the event duration as the specified time period with the bedside monitor 6, which allows a medical practitioner to modify the event duration based on their medical assessment of the patient. Moreover, the event frequency is the length of time between two activation events from the plurality of activation events. As can be seen in FIG. 27, in order to set the event frequency, the bedside monitor 6 prompts to enter a specified time period for the event frequency. If the specified time period for the event frequency is entered into the bedside monitor 6, the monitor CPU 7 then sets the event frequency as the specified time period with the bedside monitor 6, which similarly allows a medical practitioner to modify the event frequency based on their medical assessment of the patient.

Figure 28:
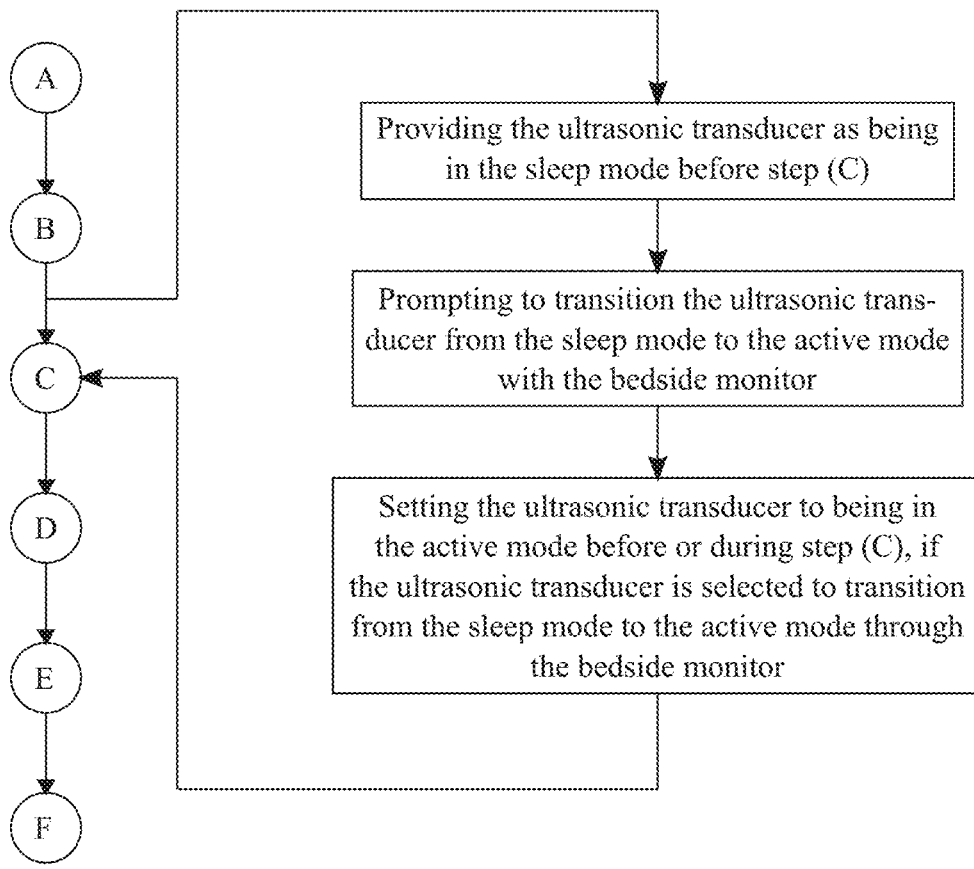
FIG. 28 is a flowchart depicting a subprocess for transitioning the ultrasound transducer from a sleep mode to an active mode based on a user's manual input.

As can be seen in FIG. 28, the third triggering subprocess transitions the ultrasonic transducer 1 from its sleep mode to its active mode based on a user input through the bedside monitor 6. For example, a medical practitioner may want to manually transition the ultrasonic transducer 1 from its sleep mode to its active mode so that the ultrasonic transducer 1 captures echocardiographic data while the medical practitioner conducts some tests on the patient. Thus, if the ultrasonic transducer 1 is in its sleep mode before Step C, the bedside monitor 6 prompts to transition the ultrasonic transducer 1 from its sleep mode to its active mode. The ultrasonic transducer 1 is then set to being in its active mode before or during Step C, if the ultrasonic transducer 1 is selected to transition from its sleep mode to its active mode through the bedside monitor 6. Once enough echocardiographic data is collected by the ultrasonic transducer 1, the ultrasonic transducer 1 can transition from its active mode to its sleep mode after a predetermined period of time, or the bedside monitor 6 can prompt to transition the ultrasonic transducer 1 from its active mode to its sleep mode, which would allow a medical practitioner to manually put the ultrasonic transducer back to its sleep mode.

Although the invention has been explained in relation to its preferred embodiment, it is to be understood that many other possible modifications and variations can be made without departing from the spirit and scope of the invention as hereinafter claimed.

What is claimed is:

1. A method of non-invasive continuous echocardiographic monitoring, the method comprising the steps of: (A) providing an adhesive pad, a pressure assistance device, an ultrasound transducer, and a bedside monitor, and wherein the bedside monitor includes a monitor central processing unit (CPU), and wherein the pressure assistance device includes a balloon and an air pump, wherein the balloon is integrated into the adhesive pad, and wherein the ultrasound transducer includes a flat body, a transducer head, a footprint, and a piezoelectric crystal arrangement, and wherein the flat body includes an outer body surface and an inner body surface, and wherein the transducer head is hingedly connected to the flat body with a projected angle set between 120 degrees to 180 degrees, and wherein the footprint and the piezoelectric crystal arrangement are integrated into the transducer head, and wherein the adhesive pad includes a first adhesive wing, a second adhesive wing, a third adhesive wing, and a fourth adhesive wing, and wherein the first adhesive wing, the second adhesive wing, the third adhesive wing, and the fourth adhesive wing are arranged into an H-shaped configuration; (B) attaching the ultrasound transducer onto a specific skin portion of a patient with the adhesive pad, positioning the balloon adjacent to the transducer head, opposite to the piezoelectric crystal arrangement, and pressing the transducer head against the specific skin portion by inflating the balloon with the air pump, wherein the specific skin portion is positioned adjacent to a heart of the patient, and wherein the first adhesive wing and the second adhesive wing are used to secure the transducer head against the specific skin portion, and wherein the third adhesive wing and the fourth adhesive wing are used to secure the flat body against the specific skin portion; (C) sensing continuous echocardiographic data with the ultrasound transducer, wherein the ultrasound transducer is set from a sleep mode to an active mode before or during sensing; (D) relaying the continuous echocardiographic data from the ultrasound transducer to the monitor CPU; (E) generating a real-time ultrasound image of the heart from the continuous echocardiographic data with the monitor CPU, wherein the real-time ultrasound image is a two-dimensional four-chamber view of the heart, a color Doppler four-chamber view of the heart, a spectral Doppler four-chamber view of the heart, or a combination thereof; and (F) outputting the real-time ultrasound image with the bedside monitor.

2. The method of non-invasive continuous echocardiographic monitoring, the method as claimed in claim 1 comprising the steps of:
providing a quantity of ultrasound gel; and
applying the quantity of ultrasound gel in between the specific skin portion and the ultrasound transducer during step (B).

3. The method of non-invasive continuous echocardiographic monitoring, the method as claimed in claim 1 being configured to orient the footprint and the piezoelectric crystal arrangement towards the flat body by situating the transducer head at a projected reverse angle with the inner body surface during step (B), wherein the projected reverse angle is set between 120 degrees to 180 degrees.

4. The method of non-invasive continuous echocardiographic monitoring, the method as claimed in claim 1 being configured to orient the footprint and the piezoelectric crystal arrangement away from the flat body by situating the transducer head at a projected forward angle with the outer body surface during step (B), wherein the projected forward angle is set between 120 degrees to 180 degrees.

5. The method of non-invasive continuous echocardiographic monitoring, the method as claimed in claim 1 comprising the steps of:
providing a coaxial cable, wherein the ultrasound transducer and the monitor CPU are communicably coupled to each other by the coaxial cable; and
relaying the continuous echocardiographic data from the ultrasound transducer, through the coaxial cable, and to the monitor CPU during step (D).

6. The method of non-invasive continuous echocardiographic monitoring, the method as claimed in claim 1 comprising the steps of:
providing the bedside monitor with a main screen;
receiving other vital signs for the patient with the monitor CPU; and
displaying the real-time ultrasound image amongst the other vital signs through a picture-in-picture visual format with the main screen during step (F).

7. The method of non-invasive continuous echocardiographic monitoring, the method as claimed in claim 1 comprising the steps of:
providing the bedside monitor with an ancillary screen; and
displaying the real-time ultrasound image with the ancillary screen during step (F).

8. The method of non-invasive continuous echocardiographic monitoring, the method as claimed in claim 1 comprising the steps of:
extrapolating at least one medical diagnosis for the heart from the continuous echocardiographic data with the monitor CPU after step (D); and
further outputting the medical diagnosis with the bedside monitor during step (F).

9. The method of non-invasive continuous echocardiographic monitoring, the method as claimed in claim 8, wherein the at least one medical diagnosis is selected from a group consisting of: cardiac function, pericardial effusion, intracardiac thrombus/vegetation, intracardiac volume, and combinations thereof.

10. The method of non-invasive continuous echocardiographic monitoring, the method as claimed in claim 1 comprising the steps of:
prompting to display the two-dimensional four-chamber view of the heart with the bedside monitor before step (F); and
outputting the two-dimensional four-chamber view of the heart with the bedside monitor during step (F), if the two-dimensional four-chamber view of the heart is selected to be displayed on the bedside monitor.

11. The method of non-invasive continuous echocardiographic monitoring, the method as claimed in claim 1 comprising the steps of:
prompting to display the color Doppler four-chamber view of the heart with the bedside monitor before step (F); and
outputting the color Doppler four-chamber view of the heart with the bedside monitor during step (F), if the color Doppler four-chamber view of the heart is selected to be displayed on the bedside monitor.

12. The method of non-invasive continuous echocardiographic monitoring, the method as claimed in claim 11, wherein the beside monitor outputs the color Doppler four-chamber view with a plurality of first flow lines and a plurality of second flow lines, and wherein the plurality of first flow lines is in a first color and is used to show blood flowing towards the ultrasound transducer, and wherein the plurality of second flow lines is in a second color and is used to show blood flowing away from the ultrasound transducer, and wherein the first color is visually contrasted by the second color.

13. The method of non-invasive continuous echocardiographic monitoring, the method as claimed in claim 1 comprising the steps of:
prompting to display the spectral Doppler four-chamber view of the heart with the bedside monitor before step (F); and
outputting the spectral Doppler four-chamber view of the heart with the bedside monitor during step (F), if the spectral Doppler four-chamber view of the heart is selected to be displayed on the bedside monitor.

14. The method of non-invasive continuous echocardiographic monitoring, the method as claimed in claim 1 comprising the steps of:
capturing a recording of the real-time ultrasound image with the monitor CPU during step (F);
prompting to replay the recording of the real-time ultrasound image with the bedside monitor after step (F); and
outputting the recording of the real-time ultrasound image with the bedside monitor, if the recording of the real-time ultrasound image is selected to be replayed by the bedside monitor.

15. The method of non-invasive continuous echocardiographic monitoring, the method as claimed in claim 1 comprising the steps of:
providing a normal ejection-fraction range managed by the monitor CPU;
deriving a real-time ejection-fraction measurement from the continuous echocardiographic data with the monitor CPU after step (D); and
outputting a life-threatening situation alert with the bedside monitor during step (F), if the real-time ejection-fraction measurement is outside of the normal ejection-fraction range.

16. The method of non-invasive continuous echocardiographic monitoring, the method as claimed in claim 15, wherein the life-threatening situation alert is outputted with the bedside monitor, if the real-time ejection-fraction measurement is less than a lower end of the normal ejection-fraction range.

17. The method of non-invasive continuous echocardiographic monitoring, the method as claimed in claim 1, wherein steps (B) through (F) are executed during a catheter interventional procedure.

18. The method of non-invasive continuous echocardiographic monitoring, the method as claimed in claim 1, wherein steps (B) through (F) are executed during a cannula placement procedure for extracorporeal membrane oxygenation.

19. The method of non-invasive continuous echocardiographic monitoring, the method as claimed in claim 1, wherein steps (B) through (F) are executed during a cannula removal procedure of extracorporeal membrane oxygenation.

20. The method of non-invasive continuous echocardiographic monitoring, the method as claimed in claim 1, wherein steps (B) through (F) are executed during a pericardiocentesis procedure.

21. The method of non-invasive continuous echocardiographic monitoring, the method as claimed in claim 1 comprising the steps of: providing at least one vital sensor, wherein the vital sensor is configured to be attached onto the patient, and wherein the vital sensor is communicably coupled to the monitor CPU, and wherein a baseline vital measurement range of the vital sensor is managed by the monitor CPU; providing the ultrasonic transducer as being in the sleep mode before step (C); capturing a current vital measurement reading with the vital sensor; sending an activation instruction from the monitor CPU to the ultrasonic transducer, if the current vital measurement reading is outside of the baseline vital measurement range; and setting the ultrasonic transducer to being in the active mode before or during step (C), once the activation instruction is received by the ultrasonic transducer.

22. The method of non-invasive continuous echocardiographic monitoring, the method as claimed in claim 21 further comprising the step of: outputting a life-threatening situation alert with the bedside monitor before or during step (C), wherein the current vital measurement reading is outside of the baseline vital measurement range.

23. The method of non-invasive continuous echocardiographic monitoring, the method as claimed in claim 21, wherein the at least one vital sensor is selected from a group consisting of an electrocardiography (ECG) sensor, an oxygen saturation sensor, a blood pressure sensor, and combinations thereof.

24. The method of non-invasive continuous echocardiographic monitoring, the method as claimed in claim 1 further comprising the steps of: providing an activation interval for the ultrasonic transducer, wherein the activation interval is managed by the monitor CPU, and wherein the activation interval includes an event duration and an event frequency; providing the ultrasonic transducer as being in the sleep mode before step (C); tracking a current date-and-time with the monitor CPU; scheduling a plurality of activation events for the ultrasonic transducer based on the event frequency with the monitor CPU, wherein each activation event includes an activation date-and-time; sending an activation instruction from the monitor CPU to the ultrasonic transducer, wherein the current date-and-time matches the activation date-and-time of an arbitrary event, and wherein the arbitrary event is any event from the plurality of activation events; setting the ultrasonic transducer to being in the active mode before or during step (C), once the activation instruction is received by the ultrasonic transducer; and resetting the ultrasonic transducer to being in the sleep mode based on the event duration.

25. The method of non-invasive continuous echocardiographic monitoring, the method as claimed in claim 24 further comprising the steps of: prompting to enter a specified time period for the event duration with the bedside monitor; and setting the event duration as the specified time period with the monitor CPU, wherein the specified time period for the event duration is entered into the bedside monitor.

26. The method of non-invasive continuous echocardiographic monitoring, the method as claimed in claim 24 further comprising the steps of: prompting to enter a specified time period for the event frequency with the bedside monitor; and setting the event frequency as the specified time period with the monitor CPU, wherein the specified time period for the event frequency is entered into the bedside monitor.

27. The method of non-invasive continuous echocardiographic monitoring, the method as claimed in claim 1 further comprising the steps of: providing the ultrasonic transducer as being in the sleep mode before step (C); prompting to transition the ultrasonic transducer from the sleep mode to the active mode with the bedside monitor; and setting the ultrasonic transducer to being in the active mode before or during step (C), wherein the ultrasonic transducer is selected to transition from the sleep mode to the active mode through the bedside monitor.

* * * * *